(12) United States Patent
Martin

(10) Patent No.: US 8,076,373 B2
(45) Date of Patent: Dec. 13, 2011

(54) METHOD FOR TREATING MAMMALIAN DISEASES AND INJURIES CAUSED BY THE OVER-EXPRESSION OF PEROXYNITRITE

(75) Inventor: Alain Martin, Ringoes, NJ (US)

(73) Assignee: North Cell Pharmacetical, Flemington, NJ (US)

( * ) Notice: Subject to any disclaimer, the term of this patent is extended or adjusted under 35 U.S.C. 154(b) by 0 days.

(21) Appl. No.: 11/056,759

(22) Filed: Feb. 11, 2005

(65) Prior Publication Data

US 2005/0197397 A1 Sep. 8, 2005

Related U.S. Application Data

(63) Continuation-in-part of application No. 10/747,963, filed on Dec. 30, 2003, now abandoned, and a continuation-in-part of application No. 10/205,354, filed on Jul. 25, 2002, now abandoned, and a continuation-in-part of application No. 09/950,490, filed on Sep. 11, 2001.

(51) Int. Cl.
*A61K 31/205* (2006.01)
*A61K 31/19* (2006.01)
*A61K 31/20* (2006.01)
*A61K 31/70* (2006.01)
*A61K 31/675* (2006.01)

(52) U.S. Cl. ........ 514/554; 514/556; 514/557; 514/558; 514/31; 514/34; 514/81

(58) Field of Classification Search .................. 514/625, 514/554, 556, 557, 558, 559, 560, 826, 851, 514/81, 6, 11, 31, 34

See application file for complete search history.

(56) References Cited

U.S. PATENT DOCUMENTS

| | | | | |
|---|---|---|---|---|
| 2,498,165 A * | 2/1950 | Johnson et al. | ............... | 435/71.3 |
| 2,565,057 A * | 8/1951 | Ainsworth et al. | ........... | 424/118 |
| 2,799,620 A * | 7/1957 | Waksman et al. | ............. | 536/13.2 |
| 3,920,835 A * | 11/1975 | Van Scott et al. | .............. | 514/460 |
| 4,199,574 A * | 4/1980 | Schaeffer | ........................ | 514/81 |
| 4,234,599 A * | 11/1980 | Van Scott et al. | .............. | 514/451 |
| 5,210,098 A * | 5/1993 | Nath | ............................ | 514/557 |
| 5,256,697 A * | 10/1993 | Miller et al. | ................... | 514/625 |
| 5,296,370 A * | 3/1994 | Martin et al. | ............... | 435/252.1 |
| 5,602,183 A | 2/1997 | Martin | | |
| 5,614,561 A | 3/1997 | Martin | | |
| 5,614,814 A | 3/1997 | Martin | | |
| 5,633,285 A * | 5/1997 | Martin | ........................ | 514/724 |
| 5,646,190 A | 7/1997 | Martin | | |
| 5,648,380 A | 7/1997 | Martin | | |
| 5,652,274 A | 7/1997 | Martin | | |
| 5,658,956 A | 8/1997 | Martin | | |
| 5,658,957 A | 8/1997 | Martin | | |
| 5,663,208 A | 9/1997 | Martin | | |
| 5,674,912 A | 10/1997 | Martin | | |
| 5,692,302 A | 12/1997 | Martin | | |
| 5,798,388 A * | 8/1998 | Katz | ............................ | 514/557 |
| 5,856,364 A | 1/1999 | Martin | | |
| 5,863,938 A * | 1/1999 | Martin | ........................ | 514/461 |
| 5,874,479 A | 2/1999 | Martin | | |
| 5,891,422 A | 4/1999 | Martin | | |
| 5,939,459 A * | 8/1999 | Katz | ............................ | 514/625 |
| 5,952,384 A * | 9/1999 | Katz | ............................ | 514/625 |
| 5,981,606 A | 11/1999 | Martin | | |
| 6,329,343 B1 | 12/2001 | Martin | | |
| 6,623,723 B2 * | 9/2003 | Katz | ............................... | 424/46 |
| 6,689,810 B2 * | 2/2004 | Martin | ........................ | 514/492 |
| 7,122,578 B2 * | 10/2006 | Martin | ........................ | 514/560 |

FOREIGN PATENT DOCUMENTS

| | | |
|---|---|---|
| WO | WO 9710818 A1 * | 3/1997 |
| WO | WO 02074301 A1 * | 9/2002 |

OTHER PUBLICATIONS

Goldman et al., Cecil, Textbook of Medicine, 21st Edition (2000), pp. 1060-1074.*

* cited by examiner

*Primary Examiner* — Kevin E Weddington
(74) *Attorney, Agent, or Firm* — Craig M. Bell

(57) ABSTRACT

The present invention provides a method for treating wounds and diseases in mammals, caused by mammalian cells involved in an inflammatory response, by altering indigenous in vivo levels of peroxynitrous acid, and salts thereof. The method comprises contacting the mammalian cells with a therapeutically effective amount of a reactive oxygen species mediator, wherein the reactive oxygen species mediator is selected from the group consisting of pyruvates, pyruvate precursors, α-keto acids having four or more carbon atoms, precursors of α-keto acids having four or more carbon atoms, and the salts thereof, wherein mediation of reactive oxygen species results in mediation of peroxynitrous acid. The present invention further provides a pharmaceutical composition for treating wounds and diseases in mammals, caused by mammalian cells involved in an inflammatory response, by altering indigenous in vivo levels of peroxynitrous acid, and salts thereof.

5 Claims, No Drawings

METHOD FOR TREATING MAMMALIAN DISEASES AND INJURIES CAUSED BY THE OVER-EXPRESSION OF PEROXYNITRITE

This application is a continuation-in-part application of U.S. patent application Ser. No. 10/747,963, filed Dec. 30, 2003 now abandoned, U.S. patent application Ser. No. 10/205,354, filed 25 Jul. 2002, now abandoned, and U.S. patent application Ser. No. 09/950,490, filed Sep. 11, 2001.

BACKGROUND OF THE INVENTION

1. Field of the Invention

The present invention provides a method for treating wounds and diseases in mammals, caused by mammalian cells involved in an inflammatory response, by altering indigenous in vivo levels of peroxynitrous acid, and salts thereof. The method comprises contacting the mammalian cells with a therapeutically effective amount of a reactive oxygen species mediator, wherein the reactive oxygen species mediator is selected from the group consisting of pyruvates, pyruvate precursors, α-keto acids having four or more carbon atoms, precursors of α-keto acids having four or more carbon atoms, and the salts thereof, wherein mediation of hydrogen peroxide results in mediation of peroxynitrous acid. The present invention further provides a pharmaceutical composition for treating wounds and diseases in mammals, caused by mammalian cells involved in an inflammatory response, by altering indigenous in vivo levels of peroxynitrous acid, and salts thereof.

2. Description of the Prior Art

The disclosures referred to herein to illustrate the background of the invention and to provide additional detail with respect to its practice are incorporated herein by reference and, for convenience, are referenced in the following text and respectively grouped in the appended bibliography.

A number of diseases are typically characterized by a marked inflammation at the site of the injury. This inflammatory process leads to further destruction of surrounding healthy tissue, and a continuation and expansion of the sites of inflammation. The over production of oxygen radicals such as hydrogen peroxide ($H_2O_2$) and peroxynitrite ($ONOO^-$) have been shown to activate both IkappaB kinase β (IKK-β) and Nuclear Factor kappa B (NF-kappa-B), both of which activate the inflammatory process in numerous diseases including cancer. Oxygen radicals, and the over-expression of inflammatory mediators controlled by NF-kappa-B will delay healing and destroy many of the medications used to treat the disease state.

Recently, it has been shown that deactivating a protein called IKK-β inside the cell stops cancer progression along with inflammation. IKK-β normally plays a role in healing (37,38,64) and directly activates NF-kappa-B. During an injury or infection, immune system molecules such as oxygen radicals, which deplete glutathione, can over-activate IKK-β (37,64). Once stimulated, IKK-β maintains cells alive and growing and can also promote inflammation in damaged tissues. IKK-β is also known to be elevated in infected epithelial cells in wounds and in diseases, including cancer. IKK-β also assists tumor growth in different types of cells by subverting the programmed cell death that would otherwise prevent tumor formation. Thus, IKK-β promotes tumor development and growth through inflammation.

IKK-β works by activating NF-kappa-B (39,40,64). NF-kappa-B resides in the cytoplasm as an inactive dimer, consisting of two subunits, bound to an inhibitory protein (44,49, 50). The inhibitory protein is degraded in response to various environmental stimuli, such as pro-inflammatory cytokines, viruses, and oxygen radicals. This degradation allows NF-kappa-B to translocate to the nucleus where it activates genes that play a role in the regulation of inflammatory responses, including genes that encode pro-inflammatory cytokines such as the interleukins (IL) including IL-2, IL-6, IL-11, and IL-17, and tumor necrosis factor (TNF).

TNF-α functions by inducing telomerase activity in the cytoplasm of cells. NF-kappa-B also regulates nitric oxide synthetase, and genes that inhibit apoptosis which play a major role in tumor growth and survival (44,49,50). NF-kappa-B also activates telomerase transcription. Telomerase repairs shortened telomere ends on chromosomes, which makes cells immortal (such as cancer cells). NF-kappa-B, when activated, stops programmed cellular death, activates other inflammatory mediators, and increases nitric oxide synthesis and production (38-40,44,64). In patients with skin diseases including infected sites and cancer, NF-kappa-B activation is exaggerated as are other inflammatory components (37,38,44). Hydrogen peroxide and other oxygen radicals, such as peroxynitrite, activate NF-kappa-B as does cellular glutathione depletion (42-45,64).

Oxygen radicals also damage p53, a protein that inhibits tumor growth. The function of p53 is to ensure that every time a cell divides, each of the two daughter cells gets an undamaged copy of the original set of genes, free of mutations. If a cell contains damaged DNA, the p53 protein stops cellular division. Only when repairs are complete, will p53 permit DNA replication to begin. If the damage is too extensive to repair, p53 blocks the cell from dividing and commands the cell to die (34). The p53 protein triggers the process of programmed cell death. In 50-80% of all cancers, p53 is damaged and does not function (34). Thus any molecule that can regulate the over-expression of peroxynitrite while protecting nitric oxide would deactivate either IKK-β or NF-kappa-B. This regulation would inhibit inflammation that could lead to tumor development and survival (41) and enhancement of the healing process of infected and noninfected wounds, with and without drugs. Antioxidants have been shown to neutralize oxygen radicals, thus inhibit NF-kappa-B activation to inhibit inflammation and to protect DNA and proteins like p53 from oxidative damage (75) thus facilitate the healing process. Antioxidants such as vitamin C, vitamin A, acetylcysteine, vitamin E, glutathione, and pyruvate down regulate and inhibit NF-kappa-B by the reduction of oxygen radicals (40-52,55,64). High levels of nitric oxide also inhibit NF-kappa-B. Thus a technology that can regulate the production of peroxynitrite and reduce NF-kappa-B induced inflammation and protect drugs needed to treat various diseases would be very useful in the therapeutic area.

Wounds are internal or external bodily injuries or lesions caused by mechanical, chemical, viral, bacterial or thermal means, which disrupt the normal continuity of structures. Such bodily injuries include contusions, which are wounds in which the skin is unbroken; incisions, i.e., which are wounds in which the skin is broken by a cutting instrument; and lacerations, which are wounds in which the skin is broken by a dull or blunt instrument.

Wound healing consists of a series of processes whereby injured tissues are repaired, specialized tissue is generated, and new tissue is reorganized. Wound healing consists of three major phases: (a) an inflammation phase (0-3 days); (b) a cellular proliferation phase (3-12 days); and (c) a remodeling phase (3-6 months).

During the inflammation phase, platelet aggregation and clotting form a matrix which traps plasma proteins and blood cells to induce the influx of various types of cells. It is at this time that peroxynitrite is produced and causes NF-kappa-B to be over-expressed, thus delaying the healing process. This over-expression of peroxynitrite can also destroy drugs needed to treat various diseases including infected wounds. During the cellular proliferation phase, new connective or granulation tissue and blood vessels are formed. During the remodeling phase, granulation tissue is replaced by a network of collagen and elastin fibers leading to the formation of scar tissue. Most wounds also produce pain, swelling, itching, ischemia, crusting, erythema, and scarring, which is caused by the over-expression of NF-kappa-B, as a result of the over-expression of peroxynitrite. Many of these adverse side-effects are caused by the reaction of over-expressed peroxynitrite with therapeutic drugs to produce undesirable metabolites.

When cells are injured or killed as a result of a wound, a wound-healing step is desirable to resuscitate the injured cells and produce new cells to replace the dead cells. Wounds require low levels of oxygen in the initial stages of healing to suppress oxidative damage and higher levels of oxygen in the later stages of healing to promote collagen formation by fibroblasts.

Wounds produce oxygen radicals. Mammalian cells are continuously exposed to activated oxygen species such as superoxide ($O_2^-$), hydrogen peroxide ($H_2O_2$), hydroxyl radicals (OH), peroxynitrite ($ONOO^-$) and singlet oxygen ($^1O_2$). In vivo, these reactive oxygen intermediates are generated by cells in response to aerobic metabolism, catabolism of drugs and other xenobiotics, ultraviolet and x-ray radiation, and the respiratory burst of phagocytic cells (such as white blood cells) to kill invading bacteria and viruses introduced through wounds. The toxic by-products generated form the catabolism of drugs to treat infected and cancerous cells activate the inflammatory process generally through the activation of NF-kappa-B, which can delay healing. Hydrogen peroxide, for example, is produced during respiration of most living organisms especially by stressed and injured cells.

These active oxygen species can injure cells. An example of such damage is lipid peroxidation which involves the oxidative degradation of unsaturated lipids. Lipid peroxidation is highly detrimental to membrane structure and function and can cause numerous cytopathological effects including the activation of NF-kappa-B. Cells defend against lipid peroxidation by producing radical scavengers such as superoxide dismutase, catalase, and peroxidase. Injured cells have a decreased ability to produce radical scavengers. Excess hydrogen peroxide, especially peroxynitrite, can react with DNA to cause backbone breakage of the DNA, produce mutations, and alteration and liberation of the bases. Hydrogen peroxide can also react with pyrimidines to open the 5, 6-double bond, which inhibits the ability of pyrimidines to hydrogen bond to complementary bases. Such oxidative biochemical injury can result in the loss of cellular membrane integrity, reduced enzyme activity, changes in transport kinetics, changes in membrane lipid content, leakage of potassium ions, amino acids, other cellular material, and the formation of excess keloid and scar formation.

Hydrogen peroxide also markedly potentiates the cytotoxic effects of eosinophil derived enzymes such as 5,8,11, 14,17-eicosapentaenoic acid (1-4,64-67). Excess superoxide anions and hydrogen peroxide, and their by-products, specifically peroxynitrite, produced during the inflammatory phase of an injury, will destroy healthy tissue surrounding the site (19). Peroxynitrite injures membranes allowing infections to spread. Oxygen radicals can also initiate lipid peroxidation employing arachidonic acid as a substrate producing prostaglandins and leukotrienes. Hydrogen peroxide can induce arachidonic acid metabolism in alveolar macrophages (10,11, 19). Hydrogen peroxide, and other oxygen radicals such as nitrogen dioxide and peroxynitrite, also activate NF-kappa-B as does cellular glutathione depletion (42-44,55,64,67-72). Oxygen radicals lower cellular levels of glutathione. Oxygen radicals also damage p53, a protein central to the inhibition of tumor growth and needed by cells to facilitate healing and DNA repair. Oxygen radicals also produce 8-isoprostanes, which are potent renal and pulmonary artery vasoconstrictors, bronchoconstrictors, and airflow obstructers (19,20,64, 66-69). Oxygen radicals, and other inflammatory mediators, specifically expressed from NF-kappa-B, will reduce the efficacy and duration of drugs needed to treat infected and noninfected wounds and cancer drugs.

Excess nitric oxide, which becomes peroxynitrite, has been implicated in inflammation (26,28,29,70). This is because nitric oxide can become a toxic oxidant when it reacts with excess oxygen radicals such as hydrogen peroxide to produce nitrogen dioxide ($NO_2$) (1-3) and peroxynitrite (ONOO). Oxygen radicals are produced by many cell types including epithelial cells, macrophages, leukocytes, monocytes, and fibroblasts. Oxygen radicals, such as superoxide ($O_2$) and hydrogen peroxide, destroy nitric oxide and produce the toxic $NO_2$ and peroxynitrite (1-3). Nitrogen dioxide causes pulmonary inflammation, lowers levels of lung antioxidants (9), including glutathione, destroys respiratory defense mechanisms, and increases susceptibility to respiratory pathogens and cancer (1,7). Nitrogen dioxide can also increase the incidence and severity of respiratory infections, can reduce lung function, and can aggravate the symptoms of asthmatics or subjects with COPD (1,8).

Peroxynitrite ion and peroxynitrous acid, formed from the interaction of nitric oxide and superoxide anions, hydroxyl radicals, and/or hydrogen peroxide, are strong oxidant species that work against nitric oxide by inducing single-strand breaks in DNA, increasing the levels of inflammatory mediators by activating NF-kappa-B and enhancing tumor formation and growth (21,64,65,71) rather than death. These properties have been demonstrated in Karposi's sarcoma in AIDS patients. Peroxynitrites are very toxic and disruptive to cell membranes via lipid peroxidation not only leading to cell death, but also dysfunction of many cellular membrane functions, such as transport mechanisms. Their effect can destroy the ability of white blood cells to kill invading microorganisms. Over-expression of peroxynitrite has been shown to destroy immune cells at the sites of infection, including CD4 and CD8 cells. Over-expression of peroxynitrite has been shown to enhance bacterial and viral replication at infected sites due to the ability of peroxynitrite to enhance NF-kappa-B expression. Peroxynitrites, which cause bronchial constriction, are involved in lung injury through the production of chemokines and contribute to viral pathogenesis and enhance viral mutations (2,3,13,30,65). Nitric oxide when combined with superoxide anions and/or hydrogen peroxide to form peroxynitrite, can also generate the highly reactive hydroxyl anion (OH), which lowers cellular levels of glutathione. The underlying chronic inflammatory process in wounds, which induces nitric oxide synthesis, also produces excess oxygen radicals, which will destroy nitric oxide (5,6). Infected and noninfected wounds enhance nitric oxide production by alveolar macrophages in rats, which also produces an increased level of oxygen radical that can react directly with nitric oxide to produce $NO_2$ and peroxynitrites. (1-3,5, 13) Peroxynitrites can also react with antimicrobial and anti-cancer drugs to destroy their ability to kill infections and cancer cells. Doxorubicin is a NF-kappa-B inducer, which dramatically increases the generation of peroxynitrite, which causes the damage produced by this drug to humans. The use of peroxynitrite inhibitors, like mercaptoethylguanidine, has been shown to reduce the damage from peroxynitrite allowing peroxynitrite treated cells to survive.

Nitric oxide, an oxidation product of nitrogen, is produced normally by many cell types, including endothelial cells and macrophages (1,2,3,12,15,16,17,26,27). Nitric oxide can act as a neurotransmitter, vasodilator, antibacterial, antiviral, and tumoricidal agent (12-18,72). Nitric oxide also possesses anti-inflammatory effects, which may be exerted via its ability to inhibit the transcription factor, NF-kappa-B (51) and other inflammatory cytokines (73). The most commonly proposed mode of action for the inhibition of NF-kappa-B involves interference with NF-kappa-B binding to DNA (53). Because IKK-β is subject to redox regulation, nitric oxide will inhibit NF-kappa-B activation by the inactivation of IKK β. High doses of nitric oxide also impaired the TNF-α-induced DNA binding activity of NF-kappa-B (55,64). High doses of nitric oxide also repressed the TNF-α induced transactivation by NF-kappa-BB (53-55) High doses of nitric oxide will inhibit NF-kappa-B. Nitric oxide also produces clinically useful bronchodilation (1) and is also used by the body to kill bacteria, fungal infections, viral infections, and tumors (21,72). Nitric oxide can kill these cell types because bacterial, viral, and tumor cells have no defenses against nitric oxide. Normal mammalian cells can cope with normal levels of nitric oxide by using enzyme systems to use or deactivate elevated cellular levels of nitric oxide (21-25). Nitric oxide is the main mediator of the tumoricidal action of activated macrophages (22-25,72).

While many papers have been written on nitric oxide, the role of nitric oxide in tumor biology was not completely understood until recently. Nitric oxide appeared to have both tumor promoting and inhibiting effects (24). Recent publications have implicated the reactive oxygen species made from nitric oxide during the inflammatory process, particularly peroxynitrite and nitrogen dioxide as being the tumor promoting agents, not nitric oxide itself (3,13,21,30). Nitric oxide does not mediate but inhibits transformation and tumor growth (72). Thus the ability to regulate the production of peroxynitrite would have tremendous therapeutic efficacy especially to protect drugs.

Sodium pyruvate, an α-keto acid, is an antioxidant that reacts directly with oxygen radicals like hydrogen peroxide and peroxynitrite, to neutralize them thereby protecting DNA and other cellular components, such as glutathione, lipids and proteins (35,56-65,70,71). In macrophages, and other cell lines, sodium pyruvate regulates the production and level of inflammatory mediators including oxygen radical production and also regulates the synthesis of nitric oxide (8,49,50). Sodium pyruvate has been administered to patients for a variety of medical disorders and applications including therapeutically and diagnostically in the treatment of Friedreich's ataxiai, and as a constituent in a therapeutic solution used in open heart surgery. It has been administered by several routes including intravenous, topical (for hyperkeratotic disorders), and oral (dietary supplements). In all cases, the administration of sodium pyruvate to these patients was shown to reduce inflammation and enhance healing. Pyruvate decreases the expression of several proinflammatory genes, including NF-kappa-B, activation of inducible nitric oxide synthase mRNA, TNF, cyclo-oxygenase, interleukin 6 and 10mRNA induction (32,33,44,49,50,64). Sodium pyruvate inhibited hydrogen peroxide induced transcription of NF-kappa-B while protecting cellular glutathione (44,64). Further, sodium pyruvate blocked the p38 MAPK pathway and activated the ERK pathway which regulates the expression of genes believed to prevent apoptosis and promote cell survival (44, 64). Sodium pyruvate inhibited hepatocytes nitric oxide synthesis (27), and caused up regulation of inducible nitric oxide synthase mRNA in intestinal cells and in cardiac monocytes (8,26,28). It can specifically lower the overproduction of superoxide anions, $H_2O_2$ and nitric oxide in white blood cells (31,56-64).

Sodium pyruvate also increases cellular levels of glutathione, a major cellular antioxidant (8), needed to prevent activation of NF-kappa-B which activates the inflammatory process. It was recently discovered that glutathione is reduced dramatically in antigen-induced asthmatic patients (10) and inhaled glutathione does not readily enter cells. Pyruvate does enter all cells via a transport system and can also cross the blood brain barrier. Oxygen radicals are involved in the induction and progression of malignancy and pyruvate, a known scavenger of oxygen radicals, has been implicated in cancer prevention (32,33,57,64).

Pyruvate inhibited the growth of implanted tumors and reduced lung metastases and decreased the number of DNA breaks caused by $H_2O_2$ by 40% (32). Excess sodium pyruvate, beyond that needed to neutralize oxygen radicals, will enter the mammalian cells. All cells have a transport system that allow cells to concentrate pyruvate at higher concentrations than serum levels. In monocytes cultures, the production of $H_2O_2$ was regulated by the level of sodium pyruvate supplied in the culture medium. At 1 mM and higher concentrations, the levels of $H_2O_2$ was decreased by 30%. At 10 mM concentrations, the levels of $H_2O_2$ was decreased by 60% (64).

Pyruvate controls the positive and negative effects of nitric oxide at higher levels. Too high a level of nitric oxide is detrimental to cells. When higher levels of nitric oxide are produced, even by activation of inducible nitric oxide synthase mRNA from higher levels of pyruvate, it is kept in control by pyruvate. Nitric oxide affects cells by increasing levels of cGMP and ADP (adenosine diphosphate), and requires an acid pH range in which to work (12). Higher levels of pyruvate raises the pH level, increases levels of ATP, decreasing levels of ADP and cAMP, and increases levels of GTP, while decreasing levels of cGMP. Thus pyruvate will protect cells from excess nitric oxide. Increased nitric oxide levels are chemotactic for eosinophils, which produce and enhance inflammation (13), especially if it is transformed into peroxynitrite. Eosinophils affect dyspnoea perception in asthma by releasing neurotoxins (13).

Inflammation is a nonspecific response caused by a variety of injuries including the penetration of the host by an infectious agent. The distinguishing feature of inflammation is the dilation and increased permeability of minute blood vessels. The inflammatory response consists of three successive phases: (a) increased vascular permeability with resulting edema, pain, and swelling, (b) cellular infiltration and phagocytoses, and (c) proliferation of the fibroblasts synthesizing new connective tissue to repair the injury. A large number of mediators of inflammation have been implicated in the inflammatory process primarily in terms of their capacity to induce vasodilation and increased permeability. Inflammation also increases levels of compounds that increase pain, erythema, ischemia, excess angiogenesis, swelling, crusting, itching, and scarring.

Direct injury, such as that caused by toxins produced by microorganisms, leads to destruction of vascular endothelium and results in the increased permeability to plasma proteins, especially in the venules and venular capillaries. Mediators of secondary injury are liberated from the site of direct injury. As a result, gaps form between vascular endothelial cells through which plasma proteins escape. Granulocytes, monocytes, and erythrocytes may also leave vascular channels. Mediators of secondary injury include unknown substances and histamine, peptides (kinins), kinin-forming enzymes (kininogenases), and a globulin permeability factor. These mediators are blocked from action by antihistamines and sympathoamines, and are most pronounced in effect on venules, although lymph-vascular endothelium also becomes more porous as a part of secondary injury. In the early stages of inflammation, the exudate is alkaline and neutrophilic polymorphonuclear leukocytes predominate. As lactic acid accumulates, presumably from glycolysis, the pH drops and macrophages become the predominant cell type. Lactic acid and antibodies in the inflammatory exudate may inhibit parasites, but the major anti-infectious effect of the inflammatory response is attributable to phagocytic cells.

The beneficial effect of the inflammatory response is the production of: (1) leukocytes in great numbers; (2) plasma proteins, nonspecific and specific humoral agents, fibrinogen that on conversion to fibrin aids in the localization of the infectious process while acting as a matrix for phagocytoses; and (3) increased blood and lymph flow that dilutes and flushes toxic materials while causing a local increase in temperature.

The initial increase in capillary permeability and vasodilation in an inflamed wound is followed by an increase in metabolism of the tissues. Leakage of fibrinogen into the wound, where proteolytic enzymes convert it into fibrin thrombi, establishes a capillary and lymphatic blockade. The concentrations of components of the ground substance of connective tissue collagen, mucopolysaccharides, glycoproteins, and nonfibrous proteins are greatly increased during this process. As the exudative phase of the inflammation subsides, the fibroblast is found to be the dominant cell in the wounded zone. The fibroblast first proliferates, then synthesizes extracellular material, including new collagen fibers and acid mucopolysaccharides, which are laid down to form the new tissue matrix.

On a macroscopic level, the inflammatory phenomenon is usually accompanied by the familiar clinical signs of erythema, swelling, edema tenderness (hyperalgesia), and pain. During this complex response, chemical mediators such as histamine, 5-hydroxytryptamine (5-HT), slow-reacting substance of anaphylaxis (SRS-A), various chemotactic factors, bradykinin, and prostaglandins are liberated locally. Phagocytic cells migrate into the area, and cellular lysosomal membranes may be ruptured, releasing lytic enzymes. All these events may contribute to the inflammatory response.

The production of reactive oxygen intermediates has been suggested to cause many skin, tissue, and organ disorders such as atherosclerosis, arthritis, cytotoxicity, skin inflammation, photoaging, wrinkling, actinic keratosis, tumor formation, cancer, hypertension, Parkinson's Disease, lung disease, and heart disease. The role of active oxygen radicals in promoting tumors has been based on the findings that (a) tumor promoters increase the level of oxygen radicals, (b) many free radical-generating systems promote tumors, and (c) certain antioxidants inhibit the biochemical effects of tumor promoters.

In vitro, reactive oxygen intermediates can be generated in cellular culture media by auto-oxidation and photo-oxidation of media components. During excision and storage, transplant organs can suffer oxidative injuries which result in the loss of cellular membrane integrity and shorten the usable life of the organ.

When cells are stressed by oxidative injury, a resuscitation step is necessary to re-condition the cells. Anti-oxidants have been shown to inhibit damage associated with active oxygen species. For example, pyruvate and other α-keto acids have been reported to react rapidly and stoichiometrically with hydrogen peroxide to protect cells from adverse cytolytic effects (61).

U.S. Pat. No. 5,210,098, issued to Nath, disclose a method to arrest or prevent acute kidney failure by administration of a non-toxic pyruvate salt to a patient in need of such treatment. Nath discloses a therapeutic method comprising the administration of an amount of a pyruvate salt to a patient experiencing or in danger of, acute renal failure. The pyruvate salt, preferably sodium pyruvate, is dispersed or dissolved in a pharmaceutically acceptable liquid carrier and administered parenterally in an amount effective to arrest or prevent the acute renal failure, thus permitting restoration of normal kidney function. In some cases, the pyruvate may be infused directly into the kidney or into the proximal renal arterial circulation. The method is effective to prevent or counteract acute kidney failure due to a wide variety of causes, including, but not limited to, traumatic injury including burn injury and obstruction; reperfusion following ischemia, inflammatory glomerulonephritis, and sepsis, e.g., due to gram negative bacterial infection.

U.S. Pat. No. 5,296,370, issued to Martin, et al., discloses therapeutic compositions for preventing and reducing injury to mammalian cells and increasing the resuscitation rate of injured mammalian cells. In one embodiment, the therapeutic composition comprises (a) a pyruvate selected from the group consisting of pyruvic acid, pharmaceutically acceptable salts of pyruvic acid, and mixtures thereof, (b) an antioxidant, and (c) a mixture of saturated and unsaturated fatty acids wherein the fatty acids are those fatty acids required for the resuscitation of injured mammalian cells.

U.S. Pat. No. 5,256,697, issued to Miller, et al., discloses a method for orally administering a therapeutically effective amount of a pyruvate precursor to a mammal to improve insulin resistance, lower lasting insulin levels and reduce fat gain.

U.S. Pat. Nos. 3,920,835; 3,984,556, and 3,988,470, all issued to Van Scott, et al. disclose methods for treating acne, dandruff, and palmar keratosis, respectively, which consist of applying to the affected area a topical composition comprising from about 1% to about 20% of a lower aliphatic compound containing from two to six carbon atoms selected from the group consisting of α-hydroxy acids, α-keto acids and esters thereof, and 3-hydroxybutryic acid in a pharmaceutically acceptable carrier. The aliphatic compounds include pyruvic acid and lactic acid.

U.S. Pat. Nos. 4,105,783 and 4,197,316, both issued to Yu, et al., disclose a method and composition, respectively, for treating dry skin which consists of applying to the affected area a topical composition comprising from about 1% to about 20% of a compound selected from the group consisting of amides and ammonium salts of α-hydroxy acids, β-hydroxy acids, and α-keto acids in a pharmaceutically acceptable carrier. The compounds include the amides and ammonium salts of pyruvic acid and lactic acid.

U.S. Pat. No. 4,234,599, issued to Van Scott, et al., discloses a method for treating actinic and non-actinic skin keratoses which consists of applying to the affected area a topical composition comprising an effective amount of a compound selected from the group consisting of α-hydroxy acids, β-hydroxy acids, and α-keto acids in a pharmaceutically acceptable carrier. The acidic compounds include pyruvic acid and lactic acid.

U.S. Pat. No. 4,294,852, issued to Wildnauer, et al., discloses a composition for treating skin which comprises the α-hydroxy acids, β-hydroxy acids, and α-keto acids disclosed above in combination with $C_3$-$C_8$ aliphatic alcohols.

U.S. Pat. No. 4,663,166, issued to Veech, discloses an electrolyte solution which comprises a mixture of L-lactate and pyruvate in a ratio from 20:1 to 1:1, respectively, or a mixture of D-β-hydroxybutyrate and acetoacetate, in a ratio from 6:1 to 0.5:1, respectively.

Sodium pyruvate has been reported to reduce the number of erosions, ulcers, and hemorrhages on the gastric mucosa in guinea pigs and rats caused by acetylsalicylic acid. The analgesic and antipyretic properties of acetylsalicylic acid were not impaired by sodium pyruvate, Puschmann, Arzneimittel-forschung, 33, pp. 410-416 (1983).

Pyruvate has been reported to exert a positive inotropic effect in stunned myocardium which is a prolonged ventricular dysfunction following brief periods of coronary artery occlusions which does not produce irreversible damage, Mentzer, et al., Ann. Surg., 209, pp. 629-633 (1989). Pyruvate has also been reported to produce a relative stabilization of left ventricular pressure and heart work parameter and to reduce the size of infarctions. Pyruvate improves resumption of spontaneous beating of the heart and restoration of normal rates and blood pressure development, Bunger, et al., J. Mol. Cell. Cardiol., 18, pp. 423-438 (1986), Mochizuki, et al., J. Physiol. (Paris), 76, pp. 805-812 (1980), Regitz, et al., Cardiovasc. Res., 15 pp. 652-658 (1981), Giannelli, et al., Ann. Thorac. Surg., 21 pp. 386-396 (1976).

Sodium pyruvate has been reported to act as an antagonist to cyanide intoxication (presumably through the formation of cyanohydrin) and to protect against the lethal effects of sodium sulfide and to retard the onset and development of functional, morphological, and biochemical measures of acrylamide neuropathy of axons, Schwartz, et al., Toxicol. Appl. Pharmacol., 50 pp. 437-442 (1979), Sabri, et al., Brain Res., 483, pp. 1-11 (1989).

U.S. Pat. No. 5,798,388, issued to Katz, discloses a method and compositions for the treatment of pulmonary diseases resulting from inflammation consisting of the administration of pyruvate, lactate, and precursor thereof and their salts in a pharmaceutically acceptable carrier. The compositions may also be a cellular energy source.

A chemotherapeutic cure of advanced L1210 leukemia has been reported using sodium pyruvate to restore abnormally deformed red blood cells to normal. The deformed red blood cells prevented adequate drug delivery to tumor cells, Cohen, Cancer Chemother. Pharmacol., 5, pp. 175-179 (1981).

Primary cultures of heterotopic tracheal transplant exposed in vivo to 7, 12-dimethylbenz(a)anthracene were reported to be successfully maintained in enrichment medium supplemented with sodium pyruvate along with the cultures of interleukin-2 stimulated peripheral blood lymphocytes, and plasmacytomas and hybridomas, pig embryos, and human blastocysts, Shacter, J. Immunol, Methods, 99, pp. 259-270 (1987), Marchok, et al., Cancer Res., 37, pp. 1811-1821 (1977), Davis, J. Reprod. Fertil, Suppl., 33, pp. 115-124 (1985), Okamoto, et al., No To Shinkei, 38, pp. 593-598 (1986), Cohen, et al., J. In vitro Fert. Embryo Transfer, 2, pp. 59-64 (1985).

U.S. Pat. Nos. 4,158,057; 4,351,835; 4,415,576, and 4,645,764, all issued to Stanko, disclose methods for preventing the accumulation of fat in the liver of a mammal due to the ingestion of alcohol, for controlling weight in a mammal, for inhibiting body fat while increasing protein concentration in a mammal, and for controlling the deposition of body fat in a living being, respectively. The methods comprise administering to the mammal a therapeutic mixture of pyruvate and dihydroxyacetone, and optionally riboflavin. U.S. Pat. No. 4,548,937, issued to Stanko, discloses a method for controlling the weight gain of a mammal which comprises administering to the mammal a therapeutically effective amount of pyruvate, and optionally riboflavin. U.S. Pat. No. 4,812,479, issued to Stanko, discloses a method for controlling the weight gain of a mammal which comprises administering to the mammal a therapeutically effective amount of dihydroxyacetone, and optionally riboflavin and pyruvate.

Rats fed a calcium-oxalate lithogenic diet including sodium pyruvate were reported to develop fewer urinary calculi (stones) than control rats not given sodium pyruvate, Ogawa, et al., Hinvokika Kivo, 32, pp. 1341-1347 (1986).

U.S. Pat. No. 4,521,375, issued to Houlsby, discloses a method for sterilizing surfaces which come into contact with living tissue. The method comprises sterilizing the surface with aqueous hydrogen peroxide and then neutralizing the surface with pyruvic acid.

U.S. Pat. No. 4,416,982, issued to Tauda, et al., discloses a method for decomposing hydrogen peroxide by reacting the hydrogen peroxide with a phenol or aniline derivative in the presence of peroxidase.

U.S. Pat. No. 4,696,917, issued to Lindstrom, et al., discloses an irrigation solution which comprises Eagle's Minimum Essential Medium with Earle's salts, chondroitin sulfate, a buffer solution, 2-mercaptoethanol, and a pyruvate. The irrigation solution may optionally contain ascorbic acid and α-tocopherol.

U.S. Pat. No. 4,725,586, also issued to Lindstrom, et al., discloses an irrigation solution which comprises a balanced salt solution, chondroitin sulfate, a buffer solution, 2-mercaptoethanol, sodium bicarbonate or dextrose, a pyruvate, a sodium phosphate buffer system, and cystine. The irrigation solution may optionally contain ascorbic acid and gamma-tocopherol.

U.S. Pat. No. 4,847,069, issued to Bissett, et al., discloses a photoprotective composition comprising (a) a sorbohydroxamic acid, (b) an anti-inflammatory agent selected from steroidal anti-inflammatory agents and a natural anti-inflammatory agent, and (c) a topical carrier. Fatty acids may be present as an emollient.

U.S. Pat. No. 4,847,071, also issued to Bissett, et al., discloses a photoprotective composition comprising (a) a tocopherol or tocopherol-ester radical scavenger, (b) an anti-inflammatory agent, and (c) a topical carrier.

U.S. Pat. No. 4,847,072, issued to Bissett, et al., discloses a topical composition comprising not more than 25% tocopherol sorbate in a topical carrier.

U.S. Pat. No. 5,863,938, issued to Martin, discloses a therapeutic antibacterial wound-healing composition comprising an effective amount of an antibacterial agent and a wound-healing composition consisting of (a) pyruvate- or α-keto-glutaric acid (b) an antioxidant, and (c) a mixture of fatty acids.

U.S. Pat. No. 5,561,157, issued to Yu, et al., discloses a composition and method for the therapeutic treatment of age spots, wrinkles, dry skin, eczema, psoriasis, and keratosis, using α- and β-keto-carboxylic acids and their salts.

U.S. Pat. No. 6,149,924, issued to Paul, discloses the use of many agents that increase the production of skin lipids, increase barrier function, hydrogen peroxide neutralization, prevention of loss of moisturizing factor from the skin. The agents are amino acids and their breakdown products.

U.S. Pat. No. 5,633,285, issued to Martin, discloses a therapeutic cytoprotective wound healing composition. The composition comprises a cytotoxic agent and a therapeutic wound healing composition which comprises (a) pyruvate (b) vitamin E, and (c) a mixture of saturated and unsaturated fatty acids. The invention is used to protect normal cells from cytotoxic drugs used in the treatment of cancer.

U.S. Pat. No. 5,536,751, issued to Bunger, discloses a pharmaceutical composition as an active phosphorylation potential enhancing substance using an α-keto-carboxylic acid, primarily pyruvate.

U.S. Pat. No. 6,689,810, issued to Martin, discloses a method for treating pulmonary disease state in mammals by altering indigenous in vivo levels of nitric oxide in mammalian cells, using α-keto acids.

U.S. patent application No. 20030165457 (Martin) discloses a method for treating wounds, injuries, diseases and dermatological disease states in mammals caused by mammalian cells involved in the inflammatory response comprising contacting the mammalian cells with an antioxidant reactive oxygen species mediator selected from the group consisting of α-keto acids used singly or in combination in an amount capable of reducing the undesired inflammatory conditions.

The addition of sodium pyruvate to bacterial and yeast systems has been reported to inhibit hydrogen peroxide production, enhance growth, and protect the systems against the toxicity of reactive oxygen intermediates. The optimum ratio of unsaturated to saturated fatty acids contained within chicken fat enhanced membrane repair and reduced cytotoxicity. The anti-oxidants gluthathione and thio-glycollate reduced the injury induced by oxygen radical species.

While the above therapeutic compositions and methods are reported to act as antioxidants that neutralize the negative effects of reactive oxygen radicals, none of the compositions and methods treat the damage and resulting disease state in mammals caused by proliferative, degenerative, cancer and infected and non-infected wounds by altering indigenous in vivo levels of peroxynitrite in mammalian cells, while protecting cells from the toxic metabolites produced by peroxynitrite. None of the therapeutic methods have devised a way to protect the drugs needed to treat these various diseases and increase their efficacy and duration. Drugs such as antivirals, antibacterials, antifungals, antitelomerases and anticancer drugs when attacked by oxygen radicals especially peroxynitrite and various inflammatory mediators controlled by NF-kappa-B will become cytotoxic compounds that will further enhance the activation of NF-kappa-B. The healing process requires the inhibition and control from the production of peroxynitrite and the reversal of cytotoxicity from the catabolism of drugs and the elimination of metabolic toxic by-products, the suppression of inflammation, including the over-expression of NF-kappa-B by these toxic by-products, the stimulation of cellular viability and proliferation. Healing also requires compounds that react directly or indirectly with toxic agents to inhibit their activation of NF-kappa-B. Patients who suffer major wounds could benefit from decreasing the over-expression of peroxynitrite and other inflammatory mediators controlled by NF-kappa-B to protect and enhance repair with and without the use medicines to reduce the pain, swelling, tissue ischemia, excess angiogenesis, erythema (redness), crusting, itching, and fibrotic conditions (scarring) which accompany most infected and non-infected wounds and cancer. This therapy will reduce undesired pain, progressive tissue ischemia, excess angiogenesis, excess white blood cell (WBC) infiltration, erythema, swelling, itching, crusting, and scarring. Moreover, cellular signaling agents in mammalian cells are needed to deposit the correct ratio and type of collagen and elastin.

SUMMARY OF THE INVENTION

The present invention provides a method for treating wounds and diseases in mammals, caused by mammalian cells involved in an inflammatory response, by altering indigenous in vivo levels of peroxynitrous acid, and salts thereof, comprising contacting the mammalian cells with a therapeutically effective amount of a reactive oxygen species mediator, wherein the reactive oxygen species mediator is selected from the group consisting of pyruvates, pyruvate precursors, α-keto acids having four or more carbon atoms, precursors of α-keto acids having four or more carbon atoms, and the salts thereof, wherein mediation of reactive oxygen species results in mediation of peroxynitrous acid.

The present invention further provides a pharmaceutical composition for treating wounds and diseases in mammals, caused by mammalian cells involved in an inflammatory response, by altering indigenous in vivo levels of peroxynitrous acid, and salts thereof, comprising a therapeutically effective amount of a reactive oxygen species mediator, wherein the reactive oxygen species mediator is selected from the group consisting of pyruvates, pyruvate precursors, α-keto acids having four or more carbon atoms, precursors of α-keto acids having four or more carbon atoms, and the salts thereof, wherein mediation of reactive oxygen species results in mediation of peroxynitrous acid.

DETAILED DESCRIPTION OF THE INVENTION

The present invention provides a method for treating wounds and diseases in mammals, caused by mammalian cells involved in an inflammatory response, by altering indigenous in vivo levels of peroxynitrous acid. The method comprises contacting the mammalian cells with a reactive oxygen species mediator selected from the group consisting of pyruvates, pyruvate precursors, α-keto acids having four or more carbon atoms, precursors of α-keto acids having four or more carbon atoms, and the salts thereof.

The present invention provides α-keto acids, such as oxaloacetate, which are reactive oxygen species mediators and which have the ability to mediate and/or down regulate the production of hydrogen peroxide. For example, oxaloacetate reacts with hydrogen peroxide to form malonate which inhibits the formation of hydrogen peroxide. Mediating the production of oxygen radicals, such as hydrogen peroxide, can alter the indigenous in vivo levels of peroxynitrous acid by protecting nitric oxide from oxygen radicals, such as hydrogen peroxide, which reacts with nitric oxide to produce peroxynitrite. By controlling the concentrations of α-keto acids in mammalian cells, the synthesis of oxygen radicals, such as hydrogen peroxide, can be mediated, which in turn can mediate levels of nitric oxide, which can be converted to peroxynitrite. The control of oxygen radicals, such as hydrogen peroxide, and nitric oxide regulates the synthesis of peroxynitrite. By decreasing the concentration of peroxynitrite at the site of injury, the level of toxic metabolites produced from the reaction of peroxynitrite and therapeutic drugs can further be decreased, thereby increasing the healing rate and efficacy of drugs used to treat disease. Reactive oxygen species mediators, which down regulate the production of hydrogen peroxide, protect nitric oxide from being converted to peroxynitrite. This down regulation of oxygen radicals, such as hydrogen peroxide, allows the production of nitric oxide to continue to thereby attack wounds and diseases.

The present invention also provides α-keto acids, such as α-keto glutarate, which have the ability to mediate and/or up regulate the production of oxygen radicals, such as hydrogen peroxide. For example, α-keto glutarate reacts with hydrogen peroxide to form succinic acid which increases the production of hydrogen peroxide. Parasites, such as worms and malaria, are more susceptible to peroxynitrite than to hydrogen peroxide and nitric oxide. Reactive oxygen species mediators, which up regulate the production of hydrogen peroxide, promote the conversion of nitric oxide to peroxynitrite. This up regulation of hydrogen peroxide promotes the production of peroxynitrite to thereby attack parasitic infections and other diseases susceptible to peroxynitrite.

As used herein, the following terms have the given meanings:

The term "cytotoxicity", as used herein, means a condition caused by a cytotoxic agent that injures the cell. Injured cells do not readily proliferate because injured cells expend all energy on cellular repair. Aiding cellular repair promotes cellular proliferation.

The term "injured cell", as used herein, means a cell that has any cellular activity disrupted for any reason. For example, an injured cell may be a cell that has injured membranes or damaged DNA, RNA, and/or ribosomes. For example, a cell which has (a) injured membranes so that transport through the membranes is diminished resulting in an increase in toxins and normal cellular wastes inside the cell and a decrease in nutrients and other components necessary for cellular repair inside the cell (b) an increase in concentration of oxygen radicals inside the cell because of the decreased ability of the cell to produce antioxidants and enzymes, or (c) damaged DNA, RNA, and ribosomes which must be repaired or replaced before normal cellular functions can be resumed.

The term "metabolite, as used herein, refers to any substance produced by metabolism or by a metabolic process. "Metabolism," as used herein, refers to the various chemical reactions involved in the transformation of molecules or chemical compounds occurring in tissue and the cells therein.

The term "pharmaceutically acceptable", as used herein, such as pharmaceutically acceptable carrier, excipient, etc. means pharmacologically acceptable and substantially non-toxic to the subject to which the particular compound is administered.

The term "pharmaceutically acceptable salt", as used herein, refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., H. Ansel et. al., Pharmaceutical Dosage Forms and Drug Delivery Systems (6th Ed. 1995) at pp. 196 and 1456-1457.

The term "prodrug", as used herein, refers to compounds, which undergo biotransformation prior to exhibiting their pharmacological effects. The chemical modification of drugs to overcome pharmaceutical problems has also been termed "drug latentiation." Drug latentiation is the chemical modification of a biologically active compound to form a new compound, which upon in vivo enzymatic attack will liberate the parent compound. The chemical alterations of the parent compound are such that the change in physicochemical properties will affect the absorption, distribution and enzymatic metabolism. The definition of drug latentiation has also been extended to include nonenzymatic regeneration of the parent compound. Regeneration takes place as a consequence of hydrolytic, dissociative, and other reactions not necessarily enzyme mediated. The terms prodrugs, latentiated drugs, and bioreversible derivatives are used interchangeably. By inference, latentiation implies a time lag element or time component involved in regenerating the bioactive parent molecule in vivo. The term prodrug is general in that it includes latentiated drug derivatives as well as those substances, which are converted after administration to the actual substance, which combines with receptors. The term prodrug is a generic term for agents, which undergo biotransformation prior to exhibiting their pharmacological actions.

The term "reactive oxygen species", as used herein, means activated oxygen species such as superoxide ($O_2^-$), hydrogen peroxide ($H_2O_2$), hydroxyl radicals (OH), and singlet oxygen ($^1O_2$). Preferably, the reactive oxygen species is superoxide and hydrogen peroxide. More preferably, the reactive oxygen species is hydrogen peroxide.

The term "reactive oxygen species mediator", as used herein, means mediators of activated oxygen species such as superoxide ($O_2^-$), hydrogen peroxide ($H_2O_2$), hydroxyl radicals (OH), and singlet oxygen ($^1O_2$). Preferably, the reactive oxygen species mediator is a mediator of superoxide and hydrogen peroxide. More preferably, the reactive oxygen species mediator is a mediator of hydrogen peroxide. In general, the reactive oxygen species mediators may be pyruvates, pyruvate precursors, α-keto acids having four or more carbon atoms, precursors of α-keto acids having four or more carbon atoms, and/or salts thereof, The term "resuscitation", as used herein, of injured mammalian cells means the reversal of cytotoxicity, the stabilization of the cellular membrane, an increase in the proliferation rate of the cell, and/or the normalization of cellular functions such as the secretion of growth factors, hormones, and the like.

The term "therapeutically effective amount", as used herein, means an amount of at least one compound of the invention, or a pharmaceutically acceptable salt thereof, which is effective to prevent, alleviate or ameliorate symptoms of disease or prolong the survival of the subject being treated. Determination of a therapeutically effective amount is within the skill in the art.

The present invention provides a method for treating wounds and diseases in mammals, caused by mammalian cells involved in an inflammatory response, by altering indigenous in vivo levels of peroxynitrous acid, and salts thereof, comprising contacting the mammalian cells with a therapeutically effective amount of a reactive oxygen species mediator, wherein the reactive oxygen species mediator is selected from the group consisting of pyruvates, pyruvate precursors, α-keto acids having four or more carbon atoms, precursors of α-keto acids having four or more carbon atoms, and the salts thereof, wherein mediation of reactive oxygen species results in mediation of peroxynitrous acid.

The present invention also provides a pharmaceutical composition for treating wounds and diseases in mammals, caused by mammalian cells involved in an inflammatory response, by altering indigenous in vivo levels of peroxynitrous acid, and salts thereof, comprising a therapeutically effective amount of a reactive oxygen species mediator, wherein the reactive oxygen species mediator is selected from the group consisting of pyruvates, pyruvate precursors, α-keto acids having four or more carbon atoms, precursors of α-keto acids having four or more carbon atoms, and the salts thereof, wherein mediation of reactive oxygen species results in mediation of peroxynitrous acid.

The cells which may be treated with the therapeutic wound-healing compositions of the present invention are mammalian cells. Although the present therapeutic wound-healing compositions are useful for treating mammalian epidermal keratinocytes and mammalian monocytes, applicant contemplates that the therapeutic wound-healing compositions may also be used to protect or resuscitate all mammalian cells. Keratinocytes are representative of normal mammalian cells and are the fastest proliferating cells in the body. The correlation between the reaction of keratinocytes to injury and therapy and that of mammalian cells in general is very high. Monocytes are representative of specialized mammalian cells such as the white blood cell in the immune system and the organ cells in liver, kidney, heart, and brain. The mammalian cells may be treated in vivo and in vitro.

Epidermal keratinocytes are the specialized epithelial cells of the epidermis which synthesize keratin, a scleroprotein which is the principal constituent of epidermis, hair, nails, horny tissue, and the organic matrix of the enamel of teeth. Mammalian epidermal keratinocytes constitute about 95% of the epidermal cells and together with melanocytes form the binary system of the epidermis. In its various successive stages, epidermal keratinocytes are also known as basal cells, prickle cells, and granular cells.

Monocytes are mononuclear phagocytic leukocytes which undergo respiratory bursting and are involved in reactive oxygen-mediated damage within the epidermis. Leukocytes are white blood count or corpuscles which may be classified into two main groups: granular leukocytes (granulocytes) which are leukocytes with abundant granules in the cytoplasm and nongranular leukocytes (nongranulocytes) which are leukocytes without specific granules in the cytoplasm and which include the lymphocytes and monocytes. Phagocytic cells are cells which ingest microorganisms or other cells and foreign particles. Monocytes are also known as large mononuclear leukocytes, and hyaline or transitional leukocytes.

Epidermal keratinocytic cells and monocytic cells have multiple oxygen generating mechanisms and the degree to which each type of mechanism functions differs in each type of cell. In monocytes, for example, the respiratory bursting process is more pronounced than in epidermal keratinocytes. Hence, the components in the therapeutic wound-healing compositions of the present invention may vary depending upon the types of cells involved in the condition being treated.

Particular disease states to be treated in the invention include infected and noninfected wounds, burns, sunburns, chemical burns, surgical procedures, psorisis, cardiovascular diseases, decubitus ulcers, diabetic ulcers, arthritis, Parkinson's disease, acquired immune deficiency syndrome (AIDS), diabetes, rheumatoid arthritis, dermatoses, inflammatory diseases, Alzheimer's disease, multiple sclerosis (MS), spinal cord injuries, cancer, organ diseases where one has damage from ischemia and reperfusion damage, i.e., brain, liver, etc., hemorrhagic shock, organ transplants, gastrointestinal disorders, aging diseases, atherosclerosis, strokes, neurological diseases, as well as any type of wound resulting from laser treatments for the removal of scar and wrinkles.

The preferred inflammatory response being reduced is selected from the group consisting of oxygen radical production, hydrogen peroxide production, cytokine and protease production, prostaglandin production, excess angiogenesis, excess white blood cell infiltration, tissue ischemia, pain, swelling, itching, crusting, erythema, histamine and leukotriene production, scar formation, and mixtures thereof.

The reactive oxygen species mediator of the present invention may be selected from the group consisting of pyruvates, pyruvate precursors, α-keto acids having four or more carbon atoms, precursors of α-keto acids having four or more carbon atoms, their pharmaceutically acceptable esters and salts, and mixtures thereof.

The pyruvates may be selected from the group consisting of pyruvic acid, lithium pyruvate, sodium pyruvate, potassium pyruvate, magnesium pyruvate, calcium pyruvate, zinc pyruvate, manganese pyruvate, ammonium pyruvate, and aluminum pyruvate. The pyruvate precursors may be selected from the group consisting of pyruvyl-glycine, pyruvyl-alanine, pyruvyl-leucine, pyruvyl-valine, pyruvyl-isoleucine, pyruvyl-phenylalanine, pyruvamide, and salts of pyruvic acid.

The α-keto acids having four or more carbon atoms may be selected from the group consisting of oxaloacetic acid, α-keto-glutaric acid, α-keto-butyric acid, α-keto-adipic acid, α-keto-caproic acid, and α-keto-isovaleric acid. The precursors of α-keto acids having four or more carbon atoms may be selected from the group consisting of α-keto acid-glycine, α-keto acid-cystine, α-keto acid-alanine, α-keto acid-leucine, α-keto acid-valine, α-keto acid-isoleucine, and α-keto acid-phenylalanine.

Pyruvic acid (2-oxopropanoic acid, α-keto propionic acid, $CH_3COCOOH$) or pyruvate is a fundamental intermediate in protein and carbohydrate metabolism and in the citric acid cycle. The citric acid cycle (tricarboxylic acid cycle, Kreb's cycle) is the major reaction sequence which executes the reduction of oxygen to generate adenosine triphosphate (ATP) by oxidizing organic compounds in respiring tissues to provide electrons to the transport system. Acetyl coenzyme A ("active acetyl") is oxidized in this process and is thereafter utilized in a variety of biological processes and is a precursor in the biosynthesis of many fatty acids and sterols. The two major sources of acetyl coenzyme A are derived from the metabolism of glucose and fatty acids. Glycolysis consists of a series of transformations wherein each glucose molecule is transformed in the cellular cytoplasm into two molecules of pyruvic acid. Pyruvic acid may then enter the mitochondria where it is oxidized by coenzyme A in the presence of enzymes and cofactors to acetyl coenzyme A. Acetyl coenzyme A can then enter the citric acid cycle.

In muscle, pyruvic acid (derived from glycogen) can be reduced to lactic acid during anerobic metabolism which can occur during exercise. Lactic acid is reoxidized and partially retransformed to glycogen during rest. Pyruvate can also act as an antioxidant to neutralize oxygen radicals in the cell and can be used in the multifunction oxidase system to reverse cytotoxicity.

The pyruvate in the present invention may be selected from the group consisting of pyruvic acid, pharmaceutically acceptable esters such as methyl, ethyl, and salts of pyruvic acid, prodrugs of pyruvic acid, and mixtures thereof. In general, the pharmaceutically acceptable salts of pyruvic acid may be alkali salts and alkaline earth salts. Preferably, the pyruvate is selected from the group consisting of pyruvic acid, lithium pyruvate, sodium pyruvate, potassium pyruvate, magnesium pyruvate, calcium pyruvate, zinc pyruvate, manganese pyruvate, methyl pyruvate, α-ketoglutaric acid, and mixtures thereof. More preferably, the pyruvate is selected from the group of salts consisting of sodium pyruvate, potassium pyruvate, magnesium pyruvate, calcium pyruvate, zinc pyruvate, manganese pyruvate, and the like, and mixtures thereof. Most preferably, the pyruvate is sodium pyruvate.

The amount of pyruvate present in the therapeutic wound healing compositions of the present invention is a therapeutically effective amount. A therapeutically effective amount of pyruvate is that amount of pyruvate necessary for the inventive composition to prevent and reduce injury to mammalian cells or increase the resuscitation rate of injured mammalian cells. The exact amount of pyruvate is a matter of preference subject to such factors as the type of condition being treated as well as the other ingredients in the composition. In a preferred embodiment, pyruvate is present in the therapeutic wound healing composition in an amount from about 10% to about 50%, preferably from about 20% to about 45%, and more preferably from about 25% to about 40%, by weight of the therapeutic wound healing composition.

A preferred α-keto acid is α-keto-isovalerate acid, $(CH_3)_2CHCOCOOH$. α-Keto-isovalerate is a fundamental intermediate in protein synthesis, i.e., the biosynthesis of the amino acids leucine, valine and their metabolism. The formation of leucine begins by condensation of α-keto-isovaleric acid (which is also the precursor of valine) with acetyl CoA to yield α-isopropylmalic acid. The subsequent steps are similar to those leading from citric acid to α-keto-glutaric acid in the tricarboxylic acid cycle. The two major sources of acetyl coenzyme A are derived from the metabolism of glucose and fatty acids. Glycolysis consists of a series of transformations wherein each glucose molecule is transformed in the cellular cytoplasm into two molecules of pyruvic acid. Pyruvic acid may then enter the mitochondria where it is oxidized by coenzyme A in the presence of enzymes and cofactors to acetyl coenzyme A. Pyruvic acid can also be converted in several steps to α-keto-isovaleric acid leading to the formation of valine.

α-Keto-isovalerate inhibits pain, erythema, itching and swelling. α-Keto-isovalerate is known to react with $H_2O_2$ to produce isobutyric acid and seems to reduce prostaglandins. α-Keto-butyrate is a superior moisturizing agent over all the other α-keto acids. α-Keto-butyrate reacts with $H_2O_2$ to produce propionic acid which has been shown to be an antifungal agent and can be used with other α-keto acids to enhance the moisture in tissues. α-Keto-glutarate is taken up by neurons and fibroblasts and therein increases neuron survival and collagen deposition by fibroblasts. In combination with pyruvate, α-keto-glutarate produced the greatest neuron survival and regeneration. α-Keto-glutarate reacts with $H_2O_2$ to produce succinic acid which inhibits mast cells from releasing histamines. α-Keto-caproate will disrupt cellular membranes and mucus. α-Keto-caproate reacts with $H_2O_2$ to produce valerate, a food source. α-Keto-caproate can be used with oxaloacetate to inhibit cancer cells from growing while at the same time allowing normal cells to grow. α-Keto-adipate dissolves excess mucus. α-Keto-adipate reacts with $H_2O_2$ to produce glutaric acid.

The α-keto-isovalerate acids of the present invention may be selected from the group consisting of α-keto-isovalerate acid, its pharmaceutically acceptable salts, pro-drugs of α-keto-isovalerate acid, and mixtures thereof. In general, the pharmaceutically acceptable salts of α-keto-isovalerate acid may be alkali salts and alkaline earth salts. Preferably, the α-keto-isovalerate is selected from the group consisting of α-keto-isovalerate acid, lithium α-keto-isovalerate, sodium α-keto-isovalerate, potassium α-keto-isovalerate, magnesium α-keto-isovalerate, calcium α-keto-isovalerate, zinc α-keto-isovalerate, manganese α-keto-isovalerate, methyl α-keto-isovalerate, and mixtures thereof. More preferably, the α-keto-isovalerate is selected from the group consisting of α-keto-isovalerate acid, lithium α-keto-isovalerate, sodium α-keto-isovalerate, and potassium most preferably, the α-keto-isovalerate is sodium α-keto-isovalerate.

The precursors of α-keto-isovalerate and the α-keto acids having four or more carbon atoms may be selected from the group consisting of a α-keto acid attached to glycine, alanine, leucine, valine, isoleucine, phenylaline, amides, or to any other amino acid or compound.

The amount of α-keto-isovalerate present in the therapeutic wound-healing compositions of the present invention is a therapeutically effective amount. A therapeutically effective amount of α-keto-isovalerate is that amount of α-keto-isovalerate necessary to prevent and reduce injury to mammalian cells and/or increase the resuscitation rate of injured mammalian cells. The exact amount of α-keto-isovalerate that is effective is a matter of preference that is determined by such factors as the type of condition being treated as well as the other ingredients incorporated in the composition. In a preferred embodiment, α-keto-isovalerate is present in the therapeutic wound-healing composition in an amount from about 0.1% to about 50%, preferably from about 0.2% to about 45%, and more preferably from about 0.5% to about 20% by weight of the therapeutic wound-healing composition.

Another preferred α-keto acid is oxaloacetic acid, $HOOCCH_2COCOOH$. It has been discovered that oxaloacetate inhibits keloid formation, angiogenesis, and excess infiltration of leukocytes. The properties of oxaloacetate can be used to prevent progressive burn ischemia due to thermal injuries which causes delayed tissue loss in surrounding healthy tissue. Oxaloacetate reacts with $H_2O_2$ to produce malonate, a competitive inhibitor of succinate dehydrogenase, which effectively inhibits respiration and the further production of $H_2O_2$ and other oxygen radicals.

Succinate, on the other hand, increases the production of hydrogen peroxide and other oxygen radicals. Malonate is effectively transported out of the mitochondria via glutathione. This is a protective method that regulates the production of hydrogen peroxide. It has been found that when oxaloacetate is used in combination with α-keto-isovalerate or pyruvate on burns, excess white blood count infiltration is reduced and healing is enhanced. Oxaloacetate can be used to treat patients undergoing radiation therapy to inhibit regrowth of the tumor, while at the same time healing normal cells.

The present invention provides the use of these α-keto acids, alone or in combination, to enhance the healing of various types of wounds. Each wound is unique and may require various types of α-keto acid combinations to treat the injuries. Not all α-keto acids are the same and each has its own unique properties. Combinations of various α-keto acids can be used to act synergistically to treat different types of wounds more successfully than their individual use to treat infected and noninfected wounds and cancer, with and without drugs, by inhibiting the over-expression of peroxynitrite.

In another preferred embodiment, the method may further comprise contacting the mammalian cells with an reactive oxygen species mediator and a therapeutic agent. The therapeutic agent may be selected from the group consisting of antibacterials, antivirals, antifungals, antitumors, antihistamines, proteins, enzymes, hormones, nonsteroidal anti-inflammatories, cytokines, and steroids. The therapeutic agent may be administered prior to administration of the reactive oxygen species mediator, concomitantly with administration of the reactive oxygen species mediator, or after administration of the reactive oxygen species mediator.

The amount of therapeutic agent present in the therapeutic compositions of the present invention is a therapeutically effective amount. A therapeutically effective amount of a therapeutic agent is the usual amount of therapeutic agent necessary to treat the particular condition. The exact amount of therapeutic agent is a matter of preference subject to such factors as the type of condition being treated as well as the other ingredients in the composition. In general, the amount of antibacterial agent present is the ordinary dosage required to obtain the desired result. Such dosages are known to the skilled practitioner in the medical arts and are not a part of the present invention. The therapeutic agent may be administered prior to administration of the reactive oxygen species mediator, concomitantly with administration of reactive oxygen species mediator, or administered after administration of reactive oxygen species mediator.

The antibacterial agents which may be employed in the therapeutic compositions may be selected from a wide variety of water-soluble and water-insoluble drugs, and their acid addition or metallic salts, useful for treating diseases produced from excess production of peroxynitrite. Both organic and inorganic salts may be used provided the antibacterial agent maintains its medicament value. The antibacterial agents may be selected from a wide range of therapeutic agents and mixtures of therapeutic agents which may be administered in sustained release or prolonged action form. Nonlimiting illustrative specific examples of antibacterial agents include bismuth containing compounds, sulfonamides; nitrofurans, metronidazole, tinidazole, nimorazole, benzoic acid; aminoglycosides, macrolides, penicillins, polypeptides, tetracyclines, cephalosporins, chloramphenicol, and clidamycin. Preferably, the antibacterial agent is selected from the group consisting of bismuth containing compounds, such as, without limitation, bismuth aluminate, bismuth subcitrate, bismuth subgalate, bismuth subsalicylate, and mixtures thereof; the sulfonamides; the nitrofurans, such as nitrofurazone, nitrofurantoin, and furozolidone; and miscellaneous antibacterials such as metronidazole, tinidazole, nimorazole, and benzoic acid; and antibiotics, including the aminoglycosides, such as gentamycin, neomycin, kanamycin, and streptomycin; the macrolides, such as erythromycin, clindamycin, and rifamycin; the penicillins, such as penicillin G, penicillin V, Ampicillin and amoxicillin; the polypeptides, such as bacitracin and polymyxin; the tetracyclines, such as tetracycline, chlorotetracycline, oxytetracycline, and doxycycline; the cephalosporins, such as cephalexin and cephalothin; and miscellaneous antibiotics, such as chloramphenicol, and clidamycin. More preferably, the antibacterial agent is selected from the group consisting of bismuth aluminate, bismuth subcitrate, bismuth subgalate, bismuth subsalicylate, sulfonamides, nitrofurazone, nitrofurantoin, furozolidone, metronidazole, tinidazole, nimorazole, benzoic acid, gentamycin, neomycin, kanamycin, streptomycin, erythromycin, clindamycin, rifamycin, penicillin G, penicillin V, Ampicillin amoxicillin, bacitracin, polymyxin, tetracycline, chlorotetracycline, oxytetracycline, doxycycline, cephalexin, cephalothin, chloramphenicol, and clidamycin.

The amount of antibacterial agent which may be employed in the therapeutic compositions of the present invention may vary depending upon the therapeutic dosage recommended or permitted for the particular antibacterial agent. In general, the amount of antibacterial agent present is the ordinary dosage required to obtain the desired result. Such dosages are known to the skilled practitioner in the medical arts and are not a part of the present invention. In a preferred embodiment, the antibacterial agent in the therapeutic composition is present in an amount from about 0.01% to about 10%, preferably from about 0.1% to about 5%, and more preferably from about 1% to about 3%, by weight.

The antiviral agents which may be employed in the therapeutic compositions may be selected from a wide variety of water-soluble and water-insoluble drugs, and their acid addition or metallic salts, useful for treating diseases produced from excess production of peroxynitrite. Both organic and inorganic salts may be used provided the antiviral agent maintains its medicament value. The antiviral agents may be selected from a wide range of therapeutic agents and mixtures of therapeutic agents which may be administered in sustained release or prolonged action form. Nonlimiting illustrative categories of such antiviral agents include RNA synthesis inhibitors, protein synthesis inhibitors, immunostimulating agents, protease inhibitors, and cytokines. Nonlimiting illustrative specific examples of such antiviral agents include the following medicaments.

(a) Acyclovir (9-[(2-hydroxyethyloxy)methyl]guanine, trade name—ZOVIRAX™) is an antiviral drug for oral administration. Acyclovir is a white, crystalline powder with a molecular weight of 225 daltons and a maximum solubility in water of 2.5 mg/mL at 37° C. Acyclovir is a synthetic purine nucleoside analogue with in vitro and in vivo inhibitory activity against human herpes viruses including herpes simplex types 1 (HSV-1) and 2 (HSV-2), varicella-zoster virus (VZV), Epstein-Barr virus (EBV), and cytomegalovirus (CMV).

(b) Foscarnet sodium (phosphonoformic acid trisodium salt, trade name—FOSCAVIR™) is an antiviral drug for intravenous administration. Foscarnet sodium is a white, crystalline powder containing 6 equivalents of water of hydration with an empirical formula of $Na_3CO_6P.6H_2O$ and a molecular weight of 300.1. Foscarnet sodium has the potential to chelate divalent metal ions such as calcium and magnesium, to form stable coordination compounds. Foscarnet sodium is an organic analogue of inorganic pyrophosphate that inhibits replication of all known herpes viruses in vitro including cytomegalovirus (CMV), herpes simplex virus types 1 and 2 (HSV-1, HSV-2), human herpes virus 6 (HHV-6), Epstein-Barr virus (EBV), and varicella-zoster virus (VZV). Foscarnet sodium exerts its antiviral activity by a selective inhibition at the pyrophosphnte binding site on virus-specific DNA polymerases and reverse transcriptases at concentrations that do not affect cellular DNA polymerases.

(c) Ribavirin (1-β-D-ribofuranosyl-1,2,4-triazole-3-carboxamide, trade name—VIRAZOLE™) is an antiviral drug provided as a sterile, lyophilized powder to be reconstituted for aerosol administration. Ribavirin is a synthetic nucleoside which is a stable, white, crystalline compound with a maximum solubility in water of 142 mg/ml at 25° C. and with only a slight solubility in ethanol. The empirical formula is $C_8H_{12}N_4O_5$ and the molecular weight is 244.2 Daltons. Ribavirin has antiviral inhibitory activity in vitro against respiratory syncytial virus, influenza virus, and herpes simplex virus. Ribavirin is also active against respiratory syncytial virus (RSV) in experimentally infected cotton rats. In cell cultures, the inhibitory activity of ribavirin for RSV is selective. The mechanism of action is unknown. Reversal of the in vitro antiviral activity by guanosine or xanthosine suggests ribavirin may act as an analogue of these cellular metabolites.

(d) Vidarabine (adenine arabinoside, Ara-A, 9-βD-arabinofuranosyladenine monohydrate, trade name—VIRA-A™) is an antiviral drug. Vidarabine is a purine nucleoside obtained from fermentation cultures of *Streptomyces* antibioticus. Vidarabine is a white, crystalline solid with the empirical formula, $C_{10}H_{13}N_5O_4.H_2O$. The molecular weight of vidarabine is 285.2, the solubility is 0.45 mg/ml at 25° C., and the melting point ranges from 260° to 270° C. Vidarabine possesses in vitro and in vivo antiviral activity against Herpes simplex virus types 1 and 2 (HSV-1 and HSV-2), and in vitro activity against varicella-zoster virus (VZV). The antiviral mechanism of action has not yet been established. Vidarabine is converted into nucleotides which inhibit viral DNA polymerase.

(e) Ganeiclovir sodium (9-(1,3-dihydroxy-2-propoxymethyl)guanine, monosodium salt, trade name—CYTOVENE™) is an antiviral drug active against cytomegalovirus for intravenous administration. Ganeiclovir sodium has a molecular formula of $C_9H_{12}N_6NaO_4$ and a molecular weight of 277.21. Ganeiclovir sodium is a white lyophilized powder with an aqueous solubility of greater than 50 mg/mL at 25° C. Ganeiclovir is a synthetic nucleoside analogue of 2'-deoxyguanosine that inhibits replication of herpes viruses both in vitro and in vivo. Sensitive human viruses include cytomegalovirus (CMV), herpes simplex virus-1 and -2 (HSV-1, HSV-2), Epstein-Barr virus (EBV), and varicella zoster virus (VZV).

(f) Zidovudine [azidothymidine (AZT), 3'-azido-3'-deoxythymidine, trade name—RETROVIR™] is an antiretroviral drug active against human immunodeficiency virus (HIV) for oral administration. Zidovudine is a white to beige, odorless, crystalline solid with a molecular weight of 267.24 daltons and a molecular formula of $C_{10}H_{13}N_5O_4$. Zidovudine is an inhibitor of the in vitro replication of some retroviruses including HIV (also known as HTLV III, LAV, or ARV). Zidovudine is a thymidine analogue in which the 3'hydroxy (—OH) group is replaced by an azido (—N3) group.

(g) Phenol (carbolic acid) is a topical antiviral, anesthetic, antiseptic, and antipruritic drug. Phenol is a colorless or white crystalline mass which is soluble in water, has a characteristic odor, a molecular formula of $C_6H_6O$, and a molecular weight of 94.11.

(h) Amantadine hydrochloride (1-adamantanamine hydrochloride, trade name—SYMMETREL™) has pharmacological actions as both an anti-Parkinson and an antiviral drug. Amantadine hydrochloride is a stable white or nearly, white crystalline powder, freely soluble in water and soluble in alcohol and in chloroform. The antiviral activity of amantadine hydrochloride against influenza A is not completely understood but the mode of action appears to be the prevention of the release of infectious viral nucleic acid into the host cell.

(i) Interferon α-n3 (human leukocyte derived, trade name—ALFERON™) is a sterile aqueous formulation of purified, natural, human interferon α-proteins for use by injection. Interferon α-n3 injection consists of interferon α-proteins comprising approximately 166 amino acids ranging in molecular weights from 16,000 to 27,000 daltons. Interferons are naturally occurring proteins with both antiviral and antiproliferative properties.

Preferred antiviral agents to be employed may be selected from the group consisting of acyclovir, foscarnet sodium, ribavirin, vidarabine, ganeiclovir sodium, zidovudine, phenol, amantadine hydrochloride, and interferon α-n3. In a preferred embodiment, the antiviral agent is selected from the group consisting of acyclovir, foscarnet sodium, ribavirin, vidarabine, and ganeiclovir sodium. In a more preferred embodiment, the antiviral agent is acyclovir.

The amount of antiviral agent which may be employed in the therapeutic compositions of the present invention may vary depending upon the therapeutic dosage recommended or permitted for the particular antiviral agent. In general, the amount of antiviral agent present is the ordinary dosage required to obtain the desired result. Such dosages are known to the skilled practitioner in the medical arts and are not a part of the present invention. In a preferred embodiment, the antiviral agent in the therpeutic composition is present in an amount from about 0.1 to about 20%, preferably from about 1 to about 10%, and more preferably from about 2% to about 7%, by weight.

The antifungal agents which may be employed in the therapeutic compositions may be selected from a wide variety of water-soluble and water-insoluble drugs, and their acid addition or metallic salts, useful for treating diseases produced from excess production of peroxynitrite. Both organic and inorganic salts may be used provided the antifungal agent maintains its medicament value. The antifungal agents may be selected from a wide range of therapeutic agents and mixtures of therapeutic agents which may be administered in sustained release or prolonged action form. Nonlimiting illustrative specific examples of antifungal agents include the following medicaments: miconazole, clotrimazole, tioconazole, terconazole, povidone-iodine, and butoconazole. Other antifungal agents are lactic acid and sorbic acid. Preferred antifungal agents are miconazole and clotrimazole.

The amount of antifungal agent which may be employed in the therapeutic compositions of the present invention may vary depending upon the therapeutic dosage recommended or permitted for the particular antifungal agent. In general, the amount of antifungal agent present is the ordinary dosage required to obtain the desired result. Such dosages are known to the skilled practitioner in the medical arts and are not a part of the present invention. In a preferred embodiment, the antifungal agent in the therapeutic composition is present in an amount from about 0.05% to about 10%, preferably from about 0.1% to about 5%, and more preferably from about 0.2% to about 4%, by weight.

The antitumor agents which may be employed in the therapeutic compositions may be selected from a wide variety of water-soluble and water-insoluble drugs, and their acid addition or metallic salts, useful for treating diseases produced from excess production of peroxynitrite. Both organic and inorganic salts may be used provided the antitumor agent maintains its medicament value. The antitumor agents may be selected from a wide range of therapeutic agents and mixtures of therapeutic agents which may be administered in sustained release or prolonged action form. Nonlimiting illustrative specific examples include anti-metabolites, antibiotics, plant products, hormones, and other miscellaneous chemotherapeutic agents. Chemically reactive drugs having nonspecific action include alkylating agents and N-alkyl-N-nitroso compounds. Examples of alkylating agents include nitrogen mustards, azridines (ethylenimines), sulfonic acid esters, and epoxides. Anti-metabolites are compounds that interfere with the formation or utilization of a normal cellular metabolite and include amino acid antagonists, vitamin and coenzyme antagonists, and antagonists of metabolites involved in nucleic acid synthesis such as glutamine antagonists, folic acid antagonists, pyrimidine antagonists, and purine antagonists. Antibiotics are compounds produced by microorganisms that have the ability to inhibit the growth of other organisms and include actinomycins and related antibiotics, glutarimide antibiotics, sarkomycin, fumagillin, streptonigrin, tenuazonic acid, actinogan, peptinogan, and anthracyclic antibiotics such as doxorubicin. Plant products include coichicine, podophyllotoxin, and vinca alkaloids. Hormones include those steroids used in breast and prostate cancer and corticosteroids used in leukemias and lymphomas. Other miscellaneous chemotherapeutic agents include urethan, hydroxyurea, and related compounds; thiosemicarbazones and related compounds; phthalanilide and related compounds; and triazenes and hydrazines. The the anticancer agent may also be a monoclonal antibody or the use of X-rays. In a preferred embodiment, the anticancer agent is an antibiotic. In a more preferred embodiment, the anticancer agent is doxorubicin. In a most preferred embodiment, the anticancer agent is doxorubicin.

The amount of antitumor agent which may be employed in the therapeutic compositions of the present invention may vary depending upon the therapeutic dosage recommended or permitted for the particular antitumor agent. In general, the amount of antitumor agent present is the ordinary dosage required to obtain the desired result. Such dosages are known to the skilled practitioner in the medical arts and are not a part of the present invention. In a preferred embodiment, the antitumor agent in the therapeutic composition is present in an amount from about 1% to about 50%, preferably from about 10% to about 30%, and more preferably from about 20% to about 25%, by weight.

In another preferred embodiment, the method may further comprise contacting the mammalian cells with an reactive oxygen species mediator and (b) an antioxidant, and (c) a mixture of saturated and unsaturated fatty acids wherein the fatty acids are those fatty acids required for the repair of cellular membranes and resuscitation of mammalian cells.

Antioxidants are substances which inhibit oxidation or suppress reactions promoted by oxygen or peroxides. Antioxidants, especially lipid-soluble antioxidants, can be absorbed into the cellular membrane to neutralize oxygen radicals and thereby protect the membrane. The antioxidants useful in the present invention may be selected from the group consisting of all forms of vitamin A (retinal), all forms of vitamin B (3,4-didehydroretinol), all forms of carotene such as α-carotene, β-carotene, gamma-carotene, σ-carotene, all forms of vitamin C (D-ascorbic acid, L-ascorbic acid), all forms of tocopherol such as vitamin E (α-tocopherol, 3,4-dihydro-2,5,7,8-tetramethyl-2-(4,8,12-trimethyltri-decyl)-2H-1-benzopyran-6-ol), (α-tocopherol, gamma-tocopherol, delta-tocopherol, tocoquinone, tocotrienol, and vitamin E esters which readily undergo hydrolysis to vitamin E such as vitamin E acetate and vitamin E succinate, and pharmaceutically acceptable vitamin E salts such as vitamin E phosphate, pro-drugs of vitamin A, carotene, vitamin C, and vitamin E, pharmaceutically acceptable salts of vitamin A, carotene, vitamin C, α-lipoic acid and vitamin E, and the like, and mixtures thereof. Preferably, the antioxidant is selected from the group of lipid-soluble antioxidants consisting of vitamin A, (carotene, vitamin E, vitamin E acetate, and mixtures thereof. More preferably, the antioxidant is vitamin E or vitamin E acetate. Most preferably, the antioxidant is vitamin E acetate.

The amount of antioxidant present in the therapeutic wound-healing compositions of the present invention is also that which is a therapeutically effective amount. A therapeutically effective amount of antioxidant is that amount of antioxidant necessary for the inventive composition to prevent and reduce injury to mammalian cells or increase the resuscitation rate of injured mammalian cells. The exact amount of antioxidant is a matter of preference subject to such factors as the type of condition being treated as well as the other ingredients in the composition. In a preferred embodiment, the antioxidant is present in the therapeutic wound-healing composition in an amount from about 0.1% to about 40%, preferably from about 0.2% to about 30%, and more preferably from about 0.5% to about 20%, by weight of the therapeutic wound-healing composition.

The mixture of saturated and unsaturated fatty acids in the present invention are those fatty acids required for the repair of mammalian cellular membranes and the production of new cells. Fatty acids are carboxylic acid compounds found in animal and vegetable fat and oil. Fatty acids are classified as lipids and are composed of chains of alkyl groups containing from 4 to 22 carbon atoms, 0-3 double bonds and characterized by a terminal carboxyl group, —COOH. Fatty acids may be saturated or unsaturated and may be solid, semisolid, or liquid. The most common saturated fatty acids are butyric acid (C4), lauric acid (C12), palmitic acid (C16), and stearic acid (C18). Unsaturated fatty acids are usually derived from vegetables and consist of alkyl chains containing from 16 to 22 carbon atoms and 0-3 double bonds with the characteristic terminal carboxyl group. The most common unsaturated fatty acids are oleic acid, linoleic acid, and linolenic acid (all C18 acids).

In general, the mixture of saturated and unsaturated fatty acids required for the repair of mammalian cellular membranes in the present invention may be derived from animal and vegetable fats and waxes, pro-drugs of saturated and unsaturated fatty acids useful in the present invention, and mixtures thereof. For example, the fatty acids in the therapeutic wound-healing composition may be in the form of mono-, di-, or trigylcerides, or free fatty acids, or mixtures thereof, which are readily available for the repair of injured cells. Cells produce the chemical components and the energy required for cellular viability and store excess energy in the form of fat. Fat is adipose tissue stored between organs of the body to furnish a reserve supply of energy. The preferred animal fats and waxes have a fatty acid composition similar to that of human fat and the fat contained in human breast milk. The preferred animal fats and waxes may be selected from the group consisting of human fat, chicken fat, cow fat (defined herein as a bovine domestic animal regardless of sex or age), sheep fat, horse fat, pig fat, and whale fat. The more preferred animal fats and waxes may be selected from the group consisting of human fat. Mixtures of other fats and waxes, such as vegetable waxes (especially sunflower oil), marine oils (especially shark liver oil), and synthetic waxes and oils, which have a fatty acid composition similar to that of animal fats and waxes, and preferably to that of human fats and waxes, may also be employed.

In a preferred embodiment, the mixture of saturated and unsaturated fatty acids has a composition similar to that of human fat and comprises the following fatty acids: butyric acid, caproic acid, caprylic acid, capric acid, lauric acid, myristic acid, myristoleic acid, palmitic acid, palmitoleic acid, stearic acid, oleic acid, linoleic acid, linolenic acid, arachidic acid, and gadoleic acid. Preferably, butyric acid, caproic acid, caprylic acid, capric acid, lauric acid, myristic acid, myristoleic acid, palmitic acid, palmitoleic acid, stearic acid, oleic acid, linoleic acid, linolenic acid, arachidic acid, and gadoleic acid are present in the mixture in about the following percentages by weight, respectively (carbon chain number and number of unsaturations are shown parenthetically, respectively): 0.2%-0.4% (C4), 0.1% (C6), 0.3%-0.8% (C8), 2.2%-3.5% (C10), 0.9%-5.5% (C12), 2.8%-8.5% (C14), 0.1%-0.6% (C14:1), 23.2%-24.6% (C16), 1.8%-3.0% (C16:1), 6.9%-9.9% (C18), 36.0%-36.5% (C18:1), 20%-20.6% (C18:2), 7.5%-7.8% (C18:3), 1.1%-4.9% (C20), and 3.3%-6.4% (C20:1).

In another preferred embodiment, the mixture of saturated and unsaturated fatty acids is typically chicken fat comprising the following fatty acids; lauric acid, myristic acid, myristoleic acid, pentadecanoic acid, palmitic acid, palmitoleic acid, margaric acid, margaroleic acid, stearic, oleic acid, linoleic acid, linolenic acid, arachidic acid, and gadoleic acid. Preferably, lauric acid, myristic acid, myristoleic acid, pentadeconoic acid, palmitic acid, palmitoleic acid, margaric acid, margaroleic acid, stearic, oleic acid, linoleic acid, linolenic acid, arachidic acid, and gadoleic acid are present in the mixture in about the following percentages by weight, respectively: 0.1% (C12), 0.8% (C14), 0.2% (C14:1), 0.1% (C15), 25.3% (C16), 7.2% (C16:1), 0.1% (C17), 0.1% (C17), 0.1% (C17:1), 6.5% (C18), 37.7% (C18:1), 20.6% (C18:2), 0.8% (C18:3), 0.2% (C20), and 0.3% (C20:1), all percentages+/− 10%.

In another preferred embodiment, the mixture of saturated and unsaturated fatty acids comprises lecithin. Lecithin (phosphatidylcholine) is a phosphatide found in all living organisms (plants and animals) and is a significant constituent of nervous tissue and brain substance. Lecithin is a mixture of the diglycerides of stearic, palmitic, and oleic acids, linked to the choline ester of phosphoric acid. The product of commerce is predominantly soybean lecithin obtained as a by-product in the manufacturing of soybean oil. Soybean Lecithin contains palmitic acid 11.7%, stearic 4.0%, palmitoleic 8.6%, oleic 9.8%, linoleic 55.0%, linolenic 4.0%, C20 to C22 acids (includes arachidonic) 5.5%. Lecithin may be represented by the formula: $CH_2OCOR—CHOCOR—CH_2O—P(O)_2—OCH_2CH_2N+(CH_3)_3$, wherein R is selected from the group consisting of stearic, palmitic, and oleic acid.

The above fatty acids and percentages thereof present in the fatty acid mixture are given as an example. The exact type of fatty acid present in the fatty acid mixture and the exact amount of fatty acid employed in the fatty acid mixture may be varied in order to obtain the result desired in the final product and such variations are now within the capabilities of those skilled in the art without the need for undue experimentation.

The amount of fatty acids present in the therapeutic wound-healing compositions of the present invention is a therapeutically effective amount. A therapeutically effective amount of fatty acids is that amount of fatty acids necessary to prevent and reduce injury to mammalian cells or increase the resuscitation rate of injured mammalian cells. The exact amount of fatty acids employed is subject to such factors as the type and distribution of fatty acids employed in the mixture, the type of condition being treated, and the other ingredients in the composition. In a preferred embodiment, the fatty acids are present in the therapeutic wound-healing composition in an amount from about 1.0% to about 50%, preferably from about 2.0% to about 45%, and more preferably from about 2.5% to about 40%, by weight of the therapeutic wound-healing composition.

This invention provides therapeutic wound-healing compositions useful for reducing the size, duration, and severity of non-infected and infected wounds and for the treatment of cancer by eliminating the toxic breakdown products from drugs and cellular metabolites that activate the inflammatory process through NF-kappa-B produced from the over production of peroxynitrite. While α-keto acids are known to be effective antioxidants that neutralize oxygen radicals which activate NF-kappa-B, it has now been discovered that these α-keto acids singly or in combination react with toxic metabolites to eliminate the metabolites directly and stop NF-kappa-B activation. The combination of certain α-keto acids regulated and reduced the levels of peroxynitrite and protected the drugs from breakdown at the target site. These therapeutic combinations also removed and eliminated the toxic breakdown products of drugs to facilitate the healing process. These therapeutic combinations facilitated the healing process, the killing of infective agents, the destruction of cancer cells, and reduced scarring, inflammation, pain, crusting, tissue ischemia, excess angiogenesis, excess white blood cell infiltration, swelling, and erythema. More particularly, the wound-healing compositions comprise an agent that enhances healing while reducing wound pain, erythema, swelling, itching, ischemia, excess white blood cell infiltration, excess angiogenesis, and crusting. This invention also provides methods for preparing and using the enhanced wound-healing compositions and the pharmaceutical compositions in which the therapeutic products may be used to protect drugs needed in infected and non-infected wounds and in cancer from the over-expression of NF-kappa-B inflammatory mediators.

Human skin produces high amounts of nitric oxide and skin cells also produce hydrogen peroxide and other oxygen radicals which cause high levels of peroxynitrite to be produced. Burned, damaged, or infected skin produces even higher levels of peroxynitrite, which damages immune cells and drugs needed to treat the damaged skin.

For example, Acyclovir is effective when taken orally or intervenously, but is not effective when taken topically to treat cold sore lesions. Infections with herpes simplex virus I (HSV-1) induces a persistent nuclear translocation of NF-kappa-B, which is dramatically enhanced by peroxynitrite. The activation of NF-kappa-B promotes efficient replication by HSV-1. In epithelial cells, HSV-1 induces NF-kappa-B causing persistent activation of NF-kappa-B, which is a critical regulator of HSV-1 replication in skin. In AIDs patients, HIV-1 also triggers and activates NF-kappa-B and AIDS patients have elevated levels of peroxynitrite, which contributes to the etiology of AIDS related dementia, persistent immunosuppression, and Kaposi's sarcoma. Peroxynitrite has also been shown to be very destructive to CD4 and CD8 cells.

It has now been discovered that α-keto acids can decrease the production and levels of peroxynitrite, while protecting nitric oxide which can enhance the viral kill rate, thereby protecting drugs like Acyclovir. For example, oxaloacetate, found predominately in mitochondria, can react with excess hydrogen peroxide and other oxygen radicals to produce malonate, which decreases cellular respiration and inhibits the excess-synthesis of hydrogen peroxide thereby lowering the production of peroxynitrite. Pyruvate increases the production of glutathione which is needed by the cells to eliminate malonate from the body. This mechanism of cellular control may be used to control the production and level of peroxynitrite needed to treat infections and protect drugs.

Hence, there is a need to reduce the levels and production of peroxynitrite, which destroys drugs and immune cells, to increase cellular levels of glutathione, to reduce inflammation in infected and noninfected wounds, to minimize damage and DNA mutations that cause diseases, and to protect drugs needed to treat these conditions by preventing their destruction and the formation of toxic agents that activate the inflammatory process. When drugs are converted into toxic metabolites, these metabolites need to be removed to stop their activation of NF-kappa-B.

There is also a need to control the growth of cancer and enhance cancer cell death (apoptosis). When IKK-β is stimulated inside a cell, IKK-β maintains cells alive and growing. Deactivating IKK-β inside a cell stops inflammation and cancer progression. It has now been discovered that toxic breakdown products from cellular metabolites and drugs can also activate NF-kappa-B and that α-keto acids will eliminate this activation process to facilitate healing. These α-keto acids singly or in combination will inhibit NF-kappa-B and thus inhibit inflammation and protect DNA and proteins such as p53 from oxidative damage. Thus applicant has discovered that drugs used to treat diseases may themselves be activators of NF-kappa-B and that their by-products, produced when treated with oxygen radicals, specifically peroxynitrite, and other inflammatory mediators will delay the healing process by the further activating NF-kappa-B.

In a preferred embodiment, the therapeutic compositions containing an reactive oxygen species mediator are administered locally to the site of inflammation. In another preferred embodiment, the therapeutic compositions are administered systemically. In yet another preferred embodiment, the therapeutic compositions are administered systemically and locally concomitantly. A most preferred method of administering the therapeutic compositions is by injection or topical application.

In a preferred embodiment, the therapeutic compositions are administered topically or by injection. Typically, the therapeutic compositions may be first applied by any suitable means. The therapeutic compositions may be in liquid or solid form or creams.

The carrier composition is selected from the group consisting of tablets, capsules, liquids, isotonic liquids, isotonic media, enteric tablets and capsules, parenterals, topicals, creams, gels, ointments, chewing gums, confections and the like.

Throughout this application, various publications have been referenced. The disclosures in these publications are incorporated herein by reference in order to more fully describe the state of the art.

REFERENCES

1. Asthma, third edition, edited by Peter Barnes, Chapter 21.
2. Moncada, S. et al., Nitric Oxide: physiology, pathophysiology, and pharmacology. 1991 Pharmacological Reviews Vol. 43, pp 109-141.
3. Nathan, C., Nitric oxide as a secretory product of mammalian cells. FASEB journal vol. Sep. 6, 1992 pp 3051-3064.
4. Rossaint, R. et al., Inhaled nitric oxide: its effect on pulmonary circulation and airway smooth muscle cells. Euro Heart Jour. 1993 vol. 14 Supp. pp 133-140.
5. Artlich, A. et al., Childhood asthma: exhaled nitric oxide in relation to clinical symptoms. Euro Respir. J. Vol. 13, pp 1395-1401.
6. Jobsis, Q. et al. Hydrogen peroxide and nitric oxide in exhaled air of children with cystic fibrosis during antibiotic treatment. Euro Respir. J. 2000 Vol. 16, pp 95-100.
7. Mukala, K. et al. Personally measured weekly exposure to $NO_2$ and respiratory health among preschool children. Euro. Respir. J. Vol. 13, pp 1411-1417.
8. Stanko R., The power of Pyruvate 1999, Keats Publishing.
9. Kelly, F. et al. Antioxidant kinetics in lung ravage fluid following exposure of humans to nitrogen dioxide. Am. J. Respir. Crit Med. Vol. 154 1991 pp 1700-1705.
10. Comhair S. et al. Rapid loss of superoxide dismutase activity during antigen induced asthmatic response. Lancet vol. 355, Feb. 19, 2000.
11. Sporn P H, et al. Hydrogen peroxide induced arachidonic acid metabolism in rat alveolar macrophage. Am Rev Respir Dis 1988 137: 49-56
12. Alving, K. Methodological aspects of exhaled nitric oxide measurements Euro Respir Rev 1999: 9:68, 208-211
13. Kharitonov, S. Exhaled nitric oxide and carbon monoxide in asthma. Euro Respir. Rev. 1999, 9:68, 212-216.
14. Gouw, P. et al. Stimuli affecting exhaled nitric oxide in asthma. Euro Respir. Rev. 1999; 9:68, 219-222.
15. Kharitonov, S. Exhaled nitric oxide and carbon monoxide in respiratory diseases. Euro Respir. Rev. 1999; 9:68, 223-226.
16. Barnes, P. The effect of drugs on exhaled nitric oxide. Euro Respir. Rev. 1999; 9:68, 231-233.
17. Baraldi, E. et al. Application of exhaled nitric oxide measurement in pediatrics. Euro Respir. Rev. 1999; 9:68, 234-240.
18. Lundberg, J. Nitric oxide in the nasal airways. Euro Respir. Rev. 1999; 9:68, 241-245.
19. Culpitt, S. The measurement of hydrogen peroxide in airways disease. Euro Respir. Rev. 1999; 9:68, 246-248.
20. Montuschi, P. Isoprostanes and other exhaled markers in respiratory diseases. Euro. Respir. Rev. 1999; 9:68, 249-253.
21. Robertson, F M, Gene expression and cellular sources of inducible nitric oxide synthase during tumor promotion. Carcinogenesis September 1996; 17 (9): 2053-9.
22. Soler M N, et al., Gene therapy of rat medullary thyroid cancer by naked nitric oxide synthase II DNA injection. J Gene Med September-October 2000; 2(5): 433-52.
23. Wang H H, B16 melanoma cell arrests in mouse liver induces nitric oxide release and sinusoidal cytotoxicity: a natural hepatic defense against metastasis. Cancer Res Oct. 15, 2000 60(20): 5862-9.
24. Brennan P A., The action and interactions of nitric oxide in solid tumors. Eur J Surg Oncol Aug. 26, 2000 (5): 434-7.
25. Gossart S. et al. Reactive oxygen intermediates as regulators of TNF-α production in rat lung inflammation induced by silica. J of Immunology 1996. 156 pp 1540-1548.
26. Oddis C V, et al. Glucose and pyruvate regulate cytokine induced nitric oxide production by cardiac monocytes. Am J Physiol. October 1996; 271 (4 Pt 1):c1244-9
27. Liang J F. et al. Role of metabolic intermediates in lipopolysaccharide cytokine mediated production of nitric oxide in isolated hepatocytes. Biochem Biophys Res Commun. Jul. 18, 1997; 236(2):379-82
28. Carvalho et al. Poster A35. Effects of nitric oxide on pulmonary hyperreactivity and airway inflammation in allergic rat models. 97th international conference 1999. American Thoracic Society
29. Taskar V. S. et al. Poster 515. Strategy for selective inhibition of human inducible nitric oxide synthase by targeting a unique epitope. 97th international conference 1999. American Thoracic Society
30. Okamoto, S. et al. Poster D42. Enhanced viral mutation by nitric oxide induced oxidative stress in sendai virus pneumonia in mice. 97th international conference. 1999. American Thoracic Society
31. Ferreira, I. M. et al. Poster 812. Effects of inhaled beclomethasone on exhaled nitric oxide as a marker of lower respiratory inflammation in patients with COPD. 97th international conference 1999. American Thoracic Society
32. Stanko, R et al. Pyruvate inhibits Growth of Mammary adenocarcinoma 13762 in rats. Research 54, 1004-1007, Feb. 15, 1994.
33. Stanko R. et al. Pyruvate inhibits clofibrate induced hepatic peroxisomal proliferation and free radical production in rats. Metabolism, vol 44, $NO_2$ (February), 1995: pp 166-171
34. Rensberger R, Gardian angle protein molecule inside the cell identified, Science, cell biology 1994.
35. Herz H, et al. Multicomponent investigation of the hydrogen peroxide and hydroxyl radical scavenging antioxidant capacities of biofluids: the roles of endogenous pyruvate and lactate. Free radical res. vol. 26, pp 19-35 1997.
36. Varkey, B, et al. Asbestosis. Medline Aug. 18, 2004.
37. Escotte, S, et al. Fluticasone reduces IL-6 and IL-8 production of cystic fibrosis bronchial epithelial cells via IKK-β kinase pathway. Euro Respir J. April 2003; 21(4): 574-81

38. Mogensen Th. et al. Activation of NF-kappa-B in virus-infected macrophages is dependent on mitochondrial oxidative stress and intercellular calcium: downstream involvement of kinases TGF-β-activated kinase 1, mitogen-activated kinase/extracellular signal-regulated kinase 1, and I kappa B kinase. J Immunol Jun. 15, 2003; 170(12): 6224-33.

39. Li, Z W. et al. IKK β is required for peripheral B cell survival and proliferation. J Immunol. May 1, 2003; 170 (9):4630-7.

40. Macotela Y. et al. 16K prolactin induces NF-kappa-B activation in pulmonary fibroblasts. J Endocrinol. December 2002; 175(3):R13-8.

41. Conron M, et al. Nuclear factor kappa B activation in alveolar macrophages requires I kappa B kinase-β, but not nuclear factor kappa B inducing kinase. Am J Respir Crit Care Med. Apr. 1, 2002 165(7):996-1004.

42. Schoonbroodt S. et al. Critical role of the amino-terminal tyrosine residue 42 and the carboxyl-terminal PEST domain of I kappa B α in NF-kappa-B activation by an oxidative stress. J Immunol Apr. 15, 2000; 164(8):4292-300

43. Torrie L J. Hydrogen peroxide-mediated inhibition of lipopolysaccharide-stimulated inhibitory kappa B kinase activity in rat aortic smooth muscle cells. Br. J Pharmacol September 2001; 134(2):393-401

44. Lee Y L. et al. Enhanced survival effect of pyruvate correlates MAPK and NF-kappa-B activation in hydrogen peroxide treated human endothelial cells. J Appl Physiol. February 2004; 96(2): 793-801.

45. Deng L, et al. 2-acetylaminofluorene up regulates rat mdrib expression through generating reactive oxygen species that activate NF-kappa-B pathway. J Biol Chem. Jan. 5, 2001; 276(1):413-20.

46. Asehnoune K. et al. Involvement of reactive oxygen species in Toll-like receptor 4-dependent activation on NF-kappa-B. J Immunol. Feb. 15, 2001; 172(4): 2522-9.

47. Lee S J. et al. Astaxanthin inhibits nitric oxide production and inflammatory gene expression by suppressing I kappa B kinase-dependent NF-kappa-B activation. Mol Cells. Aug. 31, 2003; 16(1): 97-105.

48. Carcamo J M. et al. Vitamin C ia a kinase inhibitor: dehydroascorbic acid inhibits I kappa B α kinase B. Mol Cell Biol. August 2004; 24(15):6645-52.

49. Sappington P L. et al. Ethyl pyruvate ameliorates intestinal epithelial barrier dysfunction in endotoxemic mice and immunostimulated caco-2 enterocytic monolayers. J Pharmacol. Exp Ther. January 2003; 304(1):464-76

50. Yang R. et al. Ethyl pyruvate modulates inflammatory gene expression in mice subjected to hemorrhagic shock. Am J Physiol Gastrointest liver Physiol. July 2002; 283 (1):G212-21

51. Spiecker M. et al. Differential regulation of endothelial cell adhesion molecule expression by nitric oxide donors and antioxidants. J Leukoc Biol. June 1998; (6):732-9.

52. Kang M K. et al. Protective effect of retinoic acid on interleukin-1 β-induced cytotoxicity of pancreatic β-cells. Mech Aging Dev. July 2004; 125(7):480-90.

53. Reynaert N L. et al. Nitric oxide represses inhibitory kappa B kinase through S-nitrosylation. Proc Natl Acad Sci USA. Jun. 15, 2004; 101(24):8945-50

54. Ogino S. et al. Herbimycin A abrogates nuclear factor-kappaB activation by interacting preferentially with the IkappaB kinase β subunit Mol Pharmacol. June 2004; 65(6): 1344-51.

55. Umansky V. et al. Co-stimulatory effect of nitric oxide on endothelial NF-kappa-BB implies a physiological self-amplifying mechanism Eur J Immunol. August 1998; 28(8): 2276-82

56. Giandomenico A. et al. The importance of sodium pyruvate in assessing damage produced by hydrogen peroxide. Free Radical Biol and Med. 1997 Vol 23. no 3. pp 426-434.

57. Biri H. et al. Antioxidant potential of cancerous human kidney tissues. Cancer Biochem. Biophy. 1998 vol 16 pp. 265-272

58. Wang X. et al. Pyruvate released by astrocytes protects neurons from copper catalyzed cysteine neurotoxicity. J. of Neuroscience May 15, 2001. 21(10): 3322-3331.

59. Venkataraman R. et al. Resuscitation with ethyl pyruvate solution prolongs survival and modulates plasma cytokine and nitrite-nitrate concentrations in a rat model of lipopolysaccharide-induced shock Shock. December 2002; 18(6):507-12

60. Nath K. et al. Effect of pyruvate on oxidant injury to isolated and cellular DNA. Kidney international. Vol 45 1994 pp 166-176.

61. O'Donnell-Tormey J. et al. Secretion of pyruvate. J Exp. Med. The Rockefeller Univ. press. Vol. 165 February 1987 pp 500-514.

61. Andre B et al. Pyruvate reduces anoxic injury and free radical formation in perfused rat hepatocytes. The American Physiological society. 1996 G535-G540.

63. Bassenge E. et al. Antioxidant pyruvate inhibits cardiac formation of reactive oxygen species through changes in redox state. Am J. Physiol Heart Circ Physiol 2000 279: H2431-H2438.

64. Fink M. Reactive oxygen species as mediators of organ dysfunction caused by sepsis, acute respiratory distress syndrome, or hemorrhagic shock: potential benefits of resuscitation with ringer's ethyl pyruvate solution. Curr Opin Nutr Metab Care vol 5(2) March 2002. pp 167-174

65. McBride A. et al. Superoxide dismutase and hydrogen peroxide cause rapid nitric oxide breakdown, peroxynitrite production and subsequent cell death. Biochemica et biophysica acta 1454 1999 pp 275-288

66. Dekhuijken R. et al. Increased exhalation of hydrogen peroxide in patients with stable and unstable COPD Am J Respir Crit Care Med vol 154. pp 813-16 1996.

67. Kietzmann D. et al. Hydrogen peroxide in expired breath condensate of patients with acute respiratory failure and with ARDS. Intensive Care Med. 1993 19: pp 78-81.

68. Hudson V. Rethinking cystic fibrosis pathology; the critical role of abnormal reduced glutathione transport caused by CFRT mutation. Free Rad Biol and Med. 2001. Vol 30, no 12, pp 1440-1461.

69. Rahman I. et al. Oxidative stress and regulation of glutathione in lung inflammation. Eur Respir J. 2000. 16: pp 534-554.

70. Vivar J V. et al. Peroxynitrite-mediated decarboxylation of pyruvate to both carbon dioxide and carbon dioxide radical anion. Chem. Res. Toxicol. 1997. 10, pp 786-794.

71. Schultz R. et al. Peroxynitrite impairs cardiac contractile function by decreasing cardiac efficiency. The American Physiological Society. 1997 pp H1212-H1219.

72. Dhar A. et al. Nitric oxide does not mediate by inhibits transformation and tumor phenotype. Mol Caner Ther. December 2003; 2(12): pp 1285-1293.

73. Thomassen M. et al. Nitric oxide regulation of asthmatic airway inflammation and segmental allergen challenge. J Allergy Clin Immunol vol 104, number 6 December 1999 pp 1174-1182.

74. Puhakka A et al. Modulation of DNA damage by inhibition of nitric oxide synthase and gammaglutamycysteine synthase in lung cell exposed to asbestos fibers. 2000 meeting of the Amer Thoracic Society. D42 poster B6.
75. Pan X. et al. Environmental Asbestos and Mesothelioma in California. C55 Poster E
76. Dijkstra U, F Gabreels, E. Joosetn et al. Friedrich's ataxia: Intravenous pyruvate load to demonstrate a defect in pyruvate metabolism. Neurology 1984; 34:1493-1497.
77. Giannelli S, J P McKenna, J M Bordiuk et al. Prevention of increased hemoglobin-oxygen affinity in open-heart operations with inosine-phosphate-pyruvate solution. Ann thoracic Surg 1976; 21:386-396.
78. Tsukiyama T, T Hara, M Lio et al. Preferential accumulation of 11C in human brain tumors after intravenous injection of 11C-1-pyruvate. Eur J Nucl Med; 1986: 12(5-6):244-248.
79. Companacci L, G F Guarnieri, L Faccini et al. Pyruvate tolerance test in chronic uremic patients. Nephron 1983; 10:232-237.
80. Levy S B and L A Goldsmith. Sodium pyruvate treatment for hyperkeratotic disorders. South Med J 1979; 72(5):307-310.
81. Stanko R T, R J Robertson, R-W Galbreath et al. Enhanced leg exercise endurance with a high-carbohydrate diet and dihydroxyacetone and pyruvate. J Appl Physiol 1990; 69:1651-1656.
82. Stanko R T, H R Reynolds, K D Lonchar et al. Plasma lipid concentrations in hyperlipidemic patients consuming a high-fat diet supplemented with pyruvate for 6 weeks. Am J Clin Nutr 1992: 56:950-954.
83. Stanko R T, H R Reynolds, R Hoyson et al. Pyruvate supplementation of a low-cholesterol, low-fat diet: effects on lipid concentrations and body composition in hyperlipidemic patients. Am J Clin Nutr 1994; 59:423-427.

The present invention is further illustrated by the following examples which are not intended to limit the effective scope of the claims. All parts and percentages in the examples and throughout the specification and claims are by weight of the final composition unless otherwise specified.

EXAMPLES

These examples demonstrate a comparison of the wound healing abilities of the therapeutic wound healing compositions of the present invention versus conventional wound healing compositions.

Example 1

These experiments were designed to show that therapeutic agents used to treat infections and cancer can be destroyed by the endogenous production of peroxynitrite, and that their by-products will cause the over production of peroxynitrite which will cause the over-expression of NF-kappa-B, thus delaying the healing process.

Neomycin, acyclovir, doxorubicin, and clotrimazol were placed into solutions containing peroxynitrite. One hour later the solutions were tested for peroxynitrite activity using the methods described in references 35, 65, and 70. None of the peroxynitrite solutions containing the drugs and their by-products showed any peroxynitrite activity after one hour.

When the peroxynitrite treated drugs were placed on derm-abraided skin, the drugs caused irritations due to the toxic breakdown products that were produced. The drugs also delayed healing when compared to peroxynitrite treated drugs that were tested with the addition of α-keto acids (see Tables 1-4, column 1 and 2). When peroxynitrite was tested alone on derabriaded skin, it activated inflammation and delayed healing. Peroxynitrite drug by-products are detoxified by α-keto acids and do not increase inflammation. Healing was at least 40% better with the α-keto acids.

In a second experiment, various wound sites were made on a patient's arm with strip tape which produces a shallow dermabrasion. Dermabrasion will activate the production of nitric oxide and hydrogen peroxide and generate peroxynitrite which activates NF-kappa-B which will produce inflammatory agents that will increase erythema, swelling, and delay healing. Neomycin, acyclovir, doxorubicin, and clotrimazol were tested by themselves and in combination with five α-keto acids, α-keto-isovaleric, α-keto-butyrate, oxalo-acetate, α-keto-glutarate, pyruvate, and pyruvate/keto-isovaleric, and compared (see Tables 1-4, columns A and B). Time to healing was determined visually when redness and re-epithelization occurred.

TABLE 1

| | ONOO pretreated Neomycin | | keto-isovaleric | | keto-butyrate | | oxalo-acetate | | keto-glutarate | | pyruvate | | pyruvate keto-isovaleric | |
|---|---|---|---|---|---|---|---|---|---|---|---|---|---|---|
| | 1 | 2 | A | B | A | B | A | B | A | B | A | B | A | B |
| Days to healing re-epithelization | 6 | 2.0 | 4.0 | 2.5 | 4.0 | 4.0 | 3.5 | 3.0 | 4.0 | 5.0 | 4.0 | 2.0 | 3.5 | 2.0 |
| Days of redness/erythema | 7 | 6 | 6 | 5 | 7 | 6 | 6 | 3 | 6.0 | 5 | 7 | 6 | 6 | 3 |
| Days to disappearance of swelling | 6 | 3 | 3.5 | 2.5 | 4.0 | 3 | 3.5 | 2.5 | 4.0 | 3.5 | 3.5 | 2.5 | 3.5 | 1.0 |
| Total Scores | 19 | 11 | 13.5 | 10 | 15 | 13 | 13 | 8.5 | 14 | 13.5 | 14.5 | 10.5 | 13 | 6 |
| Change from A control | | +42% | | +26% | | +14% | | +35% | | +5% | | +27% | | +54% |

1 = without pyruvate.
2 = with pyruvate.
A = petrolatum with neomycin.
B = petrolatum with drug and α-keto acid.

TABLE 2

| | ONOO pretreated Acyclovir | | keto-isovaleric | | keto-butyrate | | oxalo-acetate | | keto-glutarate | | pyruvate | | pyruvate keto-isovaleric | |
|---|---|---|---|---|---|---|---|---|---|---|---|---|---|---|
| | 1 | 2 | A | B | A | B | A | B | A | B | A | B | A | B |
| Days to healing re-epithelization | 6 | 2.0 | 5.0 | 2.5 | 4.0 | 4.0 | 4.0 | 3.0 | 5.0 | 5.0 | 5.0 | 2.0 | 5.0 | 2.0 |
| Days of redness/erythema | 8 | 6 | 6 | 5.5 | 6 | 6 | 6 | 4 | 6.0 | 3.0 | 6.0 | 6.0 | 5.0 | 3.0 |
| Days to disappearance of swelling | 4 | 2 | 4 | 3.5 | 5 | 3 | 3.5 | 2.5 | 4.0 | 3.5 | 3.5 | 2.5 | 3.5 | 2.0 |
| Total Scores | 18 | 10 | 15 | 11 | 15 | 13 | 13.5 | 9.5 | 15 | 11.5 | 14.5 | 10.5 | 13.5 | 7 |
| Change from A control | | +45% | | +26% | | +13% | | +30% | | +23% | | +28% | | +48% |

1 = without pyruvate.
2 = with pyruvate.
A = petrolatum with Acyclovir.
B = petrolatum with drug and α-keto acid.

TABLE 3

| | ONOO pretreated Doxorubicin | | keto-isovaleric | | keto-butyrate | | oxalo-acetate | | keto-glutarate | | pyruvate | | pyruvate keto-isovaleric | |
|---|---|---|---|---|---|---|---|---|---|---|---|---|---|---|
| | 1 | 2 | A | B | A | B | A | B | A | B | A | B | A | B |
| Days to healing re-epithelization | 8 | 4.0 | 7.0 | 3.5 | 7.0 | 4.0 | 8.0 | 3.0 | 6.5 | 5.0 | 7.0 | 3.0 | 7.0 | 2.5 |
| Days of redness/erythema | 11 | 6 | 7 | 5.0 | 7 | 7 | 8 | 5 | 7.0 | 7.0 | 8.0 | 5.0 | 7.0 | 3.0 |
| Days to disappearance of swelling | 7 | 4 | 4 | 2.5 | 4 | 3 | 3.5 | 2.5 | 4.0 | 3.0 | 3.5 | 2.5 | 4.0 | 2.0 |
| Total Scores | 26 | 14 | 18 | 11 | 18 | 14 | 19.5 | 10.5 | 17.5 | 15.0 | 18.5 | 10.5 | 18.0 | 7.5 |
| Change from A control | | +44% | | +39% | | +24% | | +46% | | +14% | | +43% | | +58% |

1 = without pyruvate.
2 = with pyruvate.
A = petrolatum with Doxorubicin.
B = petrolatum with drug and α-keto acid.

TABLE 4

| | ONOO pretreated Clotrimazol | | keto-isovaleric | | keto-butyrate | | oxalo-acetate | | keto-glutarate | | pyruvate | | pyruvate keto-isovaleric | |
|---|---|---|---|---|---|---|---|---|---|---|---|---|---|---|
| | 1 | 2 | A | B | A | B | A | B | A | B | A | B | A | B |
| Days to healing re-epithelization | 7 | 3.0 | 5.0 | 3.0 | 4.0 | 4.0 | 4.5 | 3.0 | 5.5 | 4.0 | 5.0 | 3.0 | 6.0 | 3.0 |
| Days of redness/erythema | 8 | 6 | 6 | 5.0 | 8 | 6 | 8 | 5 | 7.0 | 6.0 | 7.0 | 6.0 | 6.0 | 3.0 |
| Days to disappearance of swelling | 4 | 3 | 4 | 2.5 | 4 | 3 | 4.0 | 2.5 | 4.0 | 3.5 | 3.5 | 2.5 | 3.5 | 2.0 |
| Total Scores | 19 | 12 | 14 | 10.5 | 16 | 13 | 16.0 | 10.5 | 16.5 | 13.5 | 15.5 | 11.5 | 15.5 | 8.0 |
| Change from A control | | +37% | | +25% | | +19% | | +34% | | +18% | | +25% | | +48% |

1 = without pyruvate.
2 = with pyruvate.
A = petrolatum with Clotrimazol.
B = petrolatum with drug and α-keto acid.

As set out above, drugs can activate the inflammatory process through interaction with NF-kappa-B and drugs that are destroyed by peroxynitrite can produce toxic by-products that activate the inflammatory process. The data presented above show that α-keto acids can mitigate the damage produced from the toxic drug by-products and can decrease the inflammatory process thereby increasing healing. The α-keto acids reduced the healing time in all cases.

Unexpectedly, the combination of pyruvate and keto-isovalerate was synergistic and produced the best results in all categories. Oxaloacetate produced the best type of collagen deposition. Oxaloacetate when mixed with pyruvate produced unexpected results when used in combination with peroxynitrite treated doxorubicin on dermabraided skin. The results were superior to pyruvate alone. Oxaloacetate reduces the production of hydrogen peroxide produced by doxorubicin, thus reducing the production of peroxynitrite. The data illustrates that these α-keto acids mitigated the damage from drugs and the toxic metabolites of these drugs that appeared to have activated NF-kappa-B through peroxynitrite.

Example 2

This example compares the effects of 5 α-keto acids for their effects on the rate of cutaneous healing and the ability of the α-keto acids to reduce inflammation, specifically peroxynitrite at the test sites.

The wound model utilized was a split upper lip design wherein the wound was created by a well defined model of laser skin resurfacing. This model utilized pulsed $CO_2$ and Er: YAG lasers in a defined protocol (computerized scanner for $CO_2$ and uniform pulses with Er: YAG) which removes the entire stratum corneum and epidermis, as well as a uniform amount of dermis. Patient diaries were maintained to assess erythema, crusting, pain, itching, swelling, pigmentary changes, and the day of first make-up application. Blinded objective grading of improvement was independently assessed by 4 blinded observers at time intervals 3, 6, and 10 days, and 1, 2, and 4 months. Chromometer measurements of erythema were also analyzed and percentage moisture recorded A control utilized consisted of the same α-keto-wound balm without the active α-keto acid (that is pure petroleum, vitamin E, and egg yolk fatty acids). The product code is enclosed. Active agent was one of: α-keto-isovaleric acid, sodium salt; α-keto-butyric acid sodium salt; oxaloacetic acid, sodium salt; α-keto-glutaric acid, sodium salt; sodium pyruvate.

Data analysis and diary information summaries:

Moisture analysis: α-keto-butyric acid, sodium salt was by far the most effective while others had little effect on skin. This suggests that the stratum corneum barrier layer of the skin was less completely repaired than the other products (a negative).

Crusting analysis: There is a tendency for decreased duration of crusting (speed of wound healing) to be related to the length of the α-keto acids, it is possible that this is proportional to some molecular characteristic. This may also be mirrored in skin irritancy, and thus selected α-keto-isovaleric acid, sodium salt for expanded study.

Current laser skin resurfacing techniques averages 5-7 days to skin re-epithelialization (healing) whereas a few years ago, 10-14 days was typical. For ethical reasons, the selected the current "standard of care" model and thus the "delta value" for wound-healing between active and control should be greater/more significant for other types of wounds. Also, inevitably, some active contacts the control side in the upper lip model. Finally, the control, if it were plain petroleum, would have shown a greater difference. In short, these activities in all likelihood are more effective than these results show for typical "real world" wounds.

Redness: All laser wounds remain red for weeks to months, do to inflammation and the over production of peroxynitrite. The study design did not address the final redness issue in the diaries, but rather utilized a Minolta Chromometer to look at relative values of erythema. The "LAB" color space model was used wherein the "A" value correlates with erythema.

Irritation: Significant irritation would have been represented by a greater increase in the "A" value with one active compared to others. While significant differences were not noted during the study, pilot open patch testing data on known sensitive skinned individuals did show differences, some subjects developed red skin irritations and welt-like reactions (considered significant). These actives were: α-keto-glutaric acid, sodium salt and slight reaction in one person to α-keto-butyric acid, sodium salt.

Pain: The increase in pain with α-ketoglutarate was a notable event.

All 5 α-keto acid wound-healing formulations were effective in accelerating wound healing in the model and all reduced redness. Other antioxidants, such as vitamin C, vitamin E do not reduce redness and appear to be ineffective against peroxynitrite. The pyruvate formulation has proven in extended clinical usage to be an effective product. This pilot screening study provides some insight into the relative efficacy of these 5 agents. Irritation was the only adverse event. Active agent α-keto-isovaleric acid, sodium salt was selected for further evaluation in more subjects based on interpretation of this data, prior clinical experience with the pyruvate product, prior career knowledge, patch testing of the relative skin irritancy of some of these α-keto acids, and finally on the relative molecular size. Other of the activities are worthy of further clinical evaluation, in particular, α-keto-butyric acid, sodium salt and possibly oxalacetic acid, sodium salt.

Example 3

This example demonstrates the inhibition of irritation and cytotoxicity of therapeutic agents. All seven of the enumerated α-keto acids were placed into a commercially available triple antibiotic ointment (Neosporin™, containing bacitracin, 400 units, neomycin, 3.5 mg, and polymyxin B, 5,000 units in a petrolatum base) which was modified by also incorporating 4% vitamin E and 6% lecithin by weight. The α-keto acids were also placed individually into the same formula and were compared to a control consisting of the antibiotic ointment alone. Each formula was tested for healing rates and any associated irritation caused thereby on a patch of dermabraided skin. The triple antibiotic ointment without the α-keto acids produced an irritation of the skin from the antibiotics. The formulations with the α-keto acids did not. They inhibited the over production of peroxynitrite which causes the over-expression of NF-kappa-B, which reduced healing times considerably. Time in which healing took place on the skin was enhanced by three days with the α-keto acid formulations. The same antibiotics and Acyclovir were placed into solutions containing peroxynitrite then one hour later the solutions were tested for peroxynitrite, and found not to have any. When placed on dermabraided skin, they caused irritations due to the toxic breakdown products produced. When the α-keto acids were placed singly into the same solutions containing the peroxynitrite treated antimicrobials, one hour later, then tested on dermabriaded skin, no irritations were noted. The α-keto acids inhibited the toxic effects of peroxynitrite treated antimicrobials, which reduces inflammation by deactivating NF-kappa-B. When peroxynitrite is tested on derabriaded skin, it activates inflammation. When peroxynitrite is first placed in solutions containing α-keto acids, the peroxynitrite is neutralized and does not increase inflammation.

The same formula was used to treat dry winter skin, where it worked to prevent winter itch, cracking and pain. Hydrocortisone was also formulated with the α-keto acids to also treat dry skin. This formula reduced redness and pain. A commercial cold sore formula was used (Blistex™, containing allantoin, 1%, camphor, 0.5%, menthol, 0.6%, and phenol, 0.5%, in a petrolatum base) purchased and the seven enumerated α-keto acids were placed into it to treat cold sores, both as a combination and singly as well. The commercial formulation by itself was utilized as a control. The normal cold sore formulas with phenol, an antiviral agent, did not work very well. However, when α-keto acids are placed in the cold sore formulation either singly or in combination with other α-keto acids both with and without anti-oxidants and fatty acids, they heal the cold sore at a much faster rate when tested on a cold sore sufferer. The α-keto acids reduced lesion size and duration by 40% when compared to the control formula without α-keto acids.

In summary, these experiments demonstrate that α-keto acids can regulate the production and synthesis of peroxynitrite by protecting nitric oxide from other oxygen radicals like hydrogen peroxide which reacts with nitric oxide to produce peroxynitrite. By controlling the concentrations of several α-keto acids in mammalian cells, we have shown that the synthesis of nitric oxide can be controlled as well as the synthesis of hydrogen peroxide and other oxygen radicals. The control of these two oxygen radicals regulates the synthesis of peroxynitrite. By decreasing the concentrations of peroxynitrite at injury sites, we have shown that we can decrease the toxic metabolites produced from the reaction of peroxynitrite and drugs, thus increasing the healing rate as well as increasing the efficacy and duration of drugs needed to treat a specific disease.

The invention being thus described, it will be obvious that the same may be varied in many ways. Such variations are not to be regarded as a departure from the spirit and scope of the invention and all such modifications are intended to be included within the scope of the following claims.

I claim:

1. A method for treating dermabrasions, burns, dry skin and cold sores, caused by an inflammatory response in mammalian cells, by altering the indigenous in vivo levels of peroxynitrous acid, and salts therein, comprising contacting the mammalian cells with a therapeutically effective amount of a reactive oxygen species mediator, wherein the reactive oxygen species mediator is a mixture of a pyruvate or a pyruvate precursor and an α-keto acid selected from the group consisting of α-keto-glutaric acid, α-keto-isovaleric acid, their precursors, and the salts thereof, wherein the mediation of the reactive oxygen species results in mediation of peroxynitrous acid.

2. A method for treating dermabrasions, burns, dry skin and cold sores in mammals, caused by mammalian cells involved in an inflammatory response, by protecting a therapeutic antiviral agent selected from the group consisting of acyclovir, by altering indigenous in vivo levels of peroxynitrous acid, and salts thereof, comprising contacting the mammalian cells with a therapeutically effective amount of a reactive oxygen species mediator, wherein the reactive oxygen species mediator is a mixture of a pyruvate or a pyruvate precursor and an α-keto acid selected from the group consisting of α-keto-glutaric acid, α-keto-isovaleric acid, their precursors and the salts thereof, wherein mediation of the reactive oxygen species results in mediation of peroxynitrous acid.

3. A method for treating dermabrasions, burns, dry skin and cold sores in mammals, caused by mammalian cells involved in an inflammatory response, by protecting an anti-bacterial agent comprising mupirocin by altering indigenous in vivo levels of peroxynitrous acid, and salts thereof, comprising contacting the mammalian cells with a therapeutically effective amount of a reactive oxygen species mediator, wherein the reactive oxygen species mediator is a mixture of a pyruvate or a pyruvate precursor and an α-keto acid selected from the group consisting of α-keto-glutaric acid, α-keto-isovaleric acid, their precursors and the salts thereof, wherein mediation of the reactive oxygen species results in mediation of peroxynitrous acid.

4. A method for treating dermabrasions, burns, dry skin and cold sores in mammals, caused by mammalian cells involved in an inflammatory response, by protecting a therapeutic agent selected from the group consisting doxorubicin, clotrimazol, and hydrocortisone by altering indigenous in vivo levels of peroxynitrous acid, and salts thereof, comprising contacting the mammalian cells with a therapeutically effective amount of a reactive oxygen species mediator, wherein the reactive oxygen species mediator is a mixture of a pyruvate or a pyruvate precursor and an α-keto acid selected from the group consisting of a α-keto-glutaric acid, α-keto-isovaleric acid, their precursors and the salts thereof, wherein mediation of the reactive oxygen species results in mediation of peroxynitrous acid.

5. A method for treating dermabrasions, burns, dry skin and cold sores in mammals, caused by mammalian cells involved in an inflammatory response, by protecting an anti-bacterial therapeutic agent comprising a mixture of bacitracin, neomycin, and polymixin, by altering indigenous in vivo levels of peroxynitrous acid, and salts thereof, comprising contacting the mammalian cells with a therapeutically effective amount of a reactive oxygen species mediator, wherein the reactive oxygen species mediator is a mixture of a pyruvate or a pyruvate precursor and an α-keto acid selected from the group consisting of α-keto-glutaric acid, α-keto-isovaleric acid, their precursors and the salts thereof, wherein mediation of the reactive oxygen species results in mediation of peroxynitrous acid.

* * * * *